United States Patent
DePristo et al.

(10) Patent No.: US 10,354,747 B1
(45) Date of Patent: Jul. 16, 2019

(54) DEEP LEARNING ANALYSIS PIPELINE FOR NEXT GENERATION SEQUENCING

(71) Applicant: Verily Life Sciences LLC, Mountain View, CA (US)

(72) Inventors: Mark Andrew DePristo, Palo Alto, CA (US); Ryan Poplin, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 175 days.

(21) Appl. No.: 15/490,607

(22) Filed: Apr. 18, 2017

Related U.S. Application Data

(60) Provisional application No. 62/333,134, filed on May 6, 2016.

(51) Int. Cl.
  *G16B 30/00* (2019.01)
  *G06N 3/04* (2006.01)
  (Continued)

(52) U.S. Cl.
  CPC ........... *G16B 30/00* (2019.02); *G06K 9/6201* (2013.01); *G06K 9/6267* (2013.01); *G06K 9/66* (2013.01);
  (Continued)

(58) Field of Classification Search
  CPC . G06F 19/22; G06F 19/18; G06T 7/90; G06T 7/0012; G06T 2207/10024;
  (Continued)

(56) References Cited

U.S. PATENT DOCUMENTS

2016/0283655 A1* 9/2016 Ye .............................. G06F 19/18
2016/0289740 A1* 10/2016 Fu ......................... C12Q 1/6806
(Continued)

OTHER PUBLICATIONS

Zamani, Neda, et al. "Unsupervised genome-wide recognition of local relationship patterns." BMC genomics 14.1 (2013): 347. (Year : 2013).*
Lee, Wan-Ping, et al. "MOSAIK: a hash-based algorithm for accurate next-generation sequencing short-read mapping." PloS one 9.3 (2014): e90581. (Year: 2014).*

*Primary Examiner* — Jonathan S Lee
(74) *Attorney, Agent, or Firm* — McDonnell Boehnen Hulbert & Berghoff LLP

(57) ABSTRACT

A method for variant calling in a next generation sequencing analysis pipeline involves obtaining a plurality of sequence reads that each include a nucleotide aligned at a nucleotide position within a sample genome. The method also involves obtaining a plurality of alleles associated with the nucleotide position. The method further involves determining that a particular allele of the plurality of alleles matches one or more sequence reads of the plurality of sequence reads, wherein the particular allele is located at the nucleotide position. Additionally, the method involves generating an image based on information associated with the plurality of sequence reads. Further, the method involves determining, by providing the generated image to a trained neural network, a likelihood that the sample genome contains the particular allele. The method may also involves providing an output signal indicative of the determined likelihood.

20 Claims, 15 Drawing Sheets

Specification includes a Sequence Listing.

(51) Int. Cl.
  *G06K 9/66* (2006.01)
  *G06T 7/90* (2017.01)
  *G06K 9/62* (2006.01)
  *G06T 7/00* (2017.01)
  *G16B 20/00* (2019.01)

(52) U.S. Cl.
  CPC ............ *G06N 3/04* (2013.01); *G06T 7/0012* (2013.01); *G06T 7/90* (2017.01); *G16B 20/00* (2019.02); *G06T 2207/10024* (2013.01); *G06T 2207/20081* (2013.01); *G06T 2207/30072* (2013.01)

(58) Field of Classification Search
  CPC ........... G06T 2207/20081; G06T 2207/30072; G06K 9/6201; G06K 9/6267; G06K 9/66; G06N 3/04
  USPC ......................................................... 382/129
  See application file for complete search history.

(56) References Cited

U.S. PATENT DOCUMENTS

| | | | |
|---|---|---|---|
| 2016/0304954 A1* | 10/2016 | Lin | C12Q 1/6827 |
| 2017/0061072 A1* | 3/2017 | Kermani | G16B 30/00 |
| 2018/0247195 A1* | 8/2018 | Kumar | G06N 3/08 |
| 2018/0253553 A1* | 9/2018 | Ghose | G06F 21/554 |
| 2018/0276333 A1* | 9/2018 | Njie | G06F 19/18 |

* cited by examiner

| Variant Call | Likelihood of False Positive |
|---|---|
| Variant 1 | 0.9 |
| Variant 2 | 0.1 |
| Variant 3 | 0.7 |

DEEP LEARNING ANALYSIS PIPELINE FOR NEXT GENERATION SEQUENCING

CROSS-REFERENCE TO RELATED APPLICATIONS

This application claims the benefit of and incorporates by reference the content of U.S. Provisional App. No. 62/333,134, filed May 6, 2016.

BACKGROUND

Early DNA sequencing techniques, such as chain-termination methods, provided reliable solutions for reading individual DNA fragments See Sanger, F. et. al. (1977) DNA sequencing with chain-terminating inhibitors. Proc. Natl. Acad. Sci. U.S.A. 74, 5463-5467. While these first-generation technologies are effective for sequencing target genes, applying them to sequencing entire chromosomes or genomes is costly and expensive. For example, the first sequencing of a human genome—which was accomplished using the Sanger method—cost hundreds of millions of dollars and took over a decade to complete. This high cost was largely due to the sequential nature of first-generation sequencing methods; each fragment had to be individually read and manually assembled to construct a full genome.

Next generation sequencing (NGS) technologies have significantly reduced the cost of DNA sequencing by parallelizing DNA fragment reading. Some NGS methods are capable of performing millions of sequence reads concurrently, generating data for millions of base pairs in a matter of hours. See Hall, N. (2007) Advanced sequencing technologies and their wider impact in microbiology. The Journal of Experimental Biology, 209, 1518-1525. Many NGS technologies have been proposed, and employ various chemical processes, use varying read lengths, and have demonstrated various ranges of accuracy. See Metzker, M. (2010) Sequencing technologies—the next generation. Nature Reviews, Genetics, Volume 11, 31-46; see also Shendure, J. et. al. (2008) Next-generation DNA sequencing. Nature Reviews, Biotechnology, Volume 26, Number 10, 1135-1145.

NGS methods generally involve separating a DNA sample into fragments and reading the nucleotide sequence of those fragments in parallel. The resulting data generated from this process includes read data for each of those fragments, which contains a continuous sequence of nucleotide base pairs (G, A, T, C). However, while the arrangement of base pairs within a given fragment read is known, the arrangement of the fragment reads with respect to each other is not. Thus, to determine the sequence of a larger DNA strand (such as a gene or chromosome), read data from multiple fragments must be aligned. This alignment is relative to other read fragments, and may include overlapping fragments, depending upon the particular NGS method used. Some NGS methods use computational techniques and software tools to carry out read data alignment.

Accurate sequence read alignment is the first step in identifying genetic variations in a sample genome. The diverse nature of genetic variation can cause alignment algorithms and techniques to align sequence reads to incorrect locations within the genome. Furthermore, the read process used to generate sequence reads may be complex and susceptible to errors. Thus, many sequence read alignment techniques can misalign a sequence read within a genome, which can lead to incorrect detection of variants in subsequent analyses.

Once the read data has been aligned, that aligned data may be analyzed to determine the nucleotide sequence for a gene locus, gene, or an entire chromosome. However, differences in nucleotide values among overlapping read fragments may be indicative of a variant, such as a single-nucleotide polymorphism (SNP) or an insertion or deletion (INDELs), among other possible variants. For example, if read fragments that overlap at a particular locus differ, those differences might be indicative of a heterozygous SNP. As another example, if overlapping read fragments are the same at a single nucleotide, but differ from a reference genome, that gene locus or gene may be a homozygous SNP with respect to that reference genome. Accurate determination of such variants is an important aspect of genome sequencing, since those variants could represent mutations, genes that cause particular diseases, and/or otherwise serve to genotype a particular DNA sample.

The demand for high efficiency and low-cost DNA sequencing has increased in recent years. Although NGS technologies have dramatically improved upon first-generation technologies, the highly-parallelized nature of NGS techniques has presented challenges not encountered in earlier sequencing technologies. Errors in the read process can adversely impact the alignment of the resulting read data, and can subsequently lead to inaccurate sequence determinations. Furthermore, read errors can lead to erroneous detection of variants.

Currently, there are different approaches to discovering genetic variation from next-generation sequencing data. They fall, broadly, in two categories: (1) mapping-based approaches which rely on a sophisticated aligner to place the reads properly on the genome (e.g., Samtools and Free-Bayes) and, (2) assembly-based approaches which attempt to discover new haplotypes in the reads by assembling them into various types of graphs (e.g., HaplotypeCaller and Platypus). Because none of the current approaches are capable of a detail given such unique data, there exists a need for a method of identifying and quantifying genomic data.

A more comprehensive and accurate understanding of both the human genome as a whole and the genomes of individuals will improve medical diagnoses and treatment. NGS technologies have reduced the time and cost of sequencing an individual's genome, which provides the potential for significant improvements to medicine and genetics in ways that were previously not feasible. Understanding genetic variation among humans provides a framework for understanding genetic disorders and Mendelian diseases. However, discovering these genetic variations depends upon reliable read data and accurate read sequence alignment.

SUMMARY

The present disclosure generally relates to variant calling in a next generation sequencing analysis pipeline. In one example, a method is disclosed. The method involves obtaining a plurality of sequence reads that each include a nucleotide aligned at a nucleotide position within a sample genome. The method also involves obtaining a plurality of alleles associated with the nucleotide position. The method further involves determining that a particular allele of the plurality of alleles matches one or more sequence reads of the plurality of sequence reads, wherein the particular allele is located at the nucleotide position. Additionally, the method involves generating an image based on information associated with the plurality of sequence reads. Further, the method involves determining, by providing the generated image to a trained neural network, a likelihood that the sample genome contains the particular allele. The method may also involves providing an output signal indicative of the determined likelihood.

In still another example, a method is disclosed. The method involves obtaining a plurality of sequence reads that each include a nucleotide aligned at a nucleotide position within a sample genome. The sequence reads are aligned to a reference genome according to a first alignment. The method also involves receiving a variant call at the nucleotide position and associated with the sample genome. The variant call includes a first confidence value indicative of a likelihood that the sample genome contains a variant specified by the variant call at the nucleotide position. The method further involves determining that the nucleotide position is located within a region of ambiguity. Additionally, the method involves realigning one or more sequence reads of the plurality of sequence reads based on the determination that the nucleotide position is located within the region of ambiguity. The realignment causes the sequence reads to be aligned to the reference genome according to a second alignment. Further, the method includes providing an output signal indicative of the second alignment.

In still another example, a non-transitory computer-readable medium is disclosed. The non-transitory computer-readable medium has instructions stored thereon that, upon execution by at least one processor, causes performance of a set of operations. The operations include obtaining a plurality of sequence reads that each include a nucleotide aligned at a nucleotide position within a sample genome. The operations also include obtaining a plurality of alleles associated with the nucleotide position. The operations further include determining that a particular allele of the plurality of alleles matches one or more sequence reads of the plurality of sequence reads, wherein the particular allele is located at the nucleotide position. Additionally, the operations include generating an image based on information associated with the plurality of sequence reads. Further, the operations include determining, by providing the generated image to a trained neural network, a likelihood that the sample genome contains the particular allele. The operations may also include providing an output signal indicative of the determined likelihood.

In yet another example, a system is disclosed. The system includes a means for obtaining a plurality of sequence reads that each include a nucleotide aligned at a nucleotide position within a sample genome. The system also includes a means for obtaining a plurality of alleles associated with the nucleotide position. The system further includes a means for determining that a particular allele of the plurality of alleles matches one or more sequence reads of the plurality of sequence reads, wherein the particular allele is located at the nucleotide position. Additionally, the system includes a means for generating an image based on information associated with the plurality of sequence reads. Further, the system includes a means for determining, by providing the generated image to a trained neural network, a likelihood that the sample genome contains the particular allele. The system may also include a means for providing an output signal indicative of the determined likelihood.

The foregoing summary is illustrative only and is not intended to be in any way limiting. In addition to the illustrative aspects, embodiments, and features described above, further aspects, embodiments, and features will become apparent by reference to the figures and the following detailed description and the accompanying drawings.

DETAILED DESCRIPTION

Figure 1:
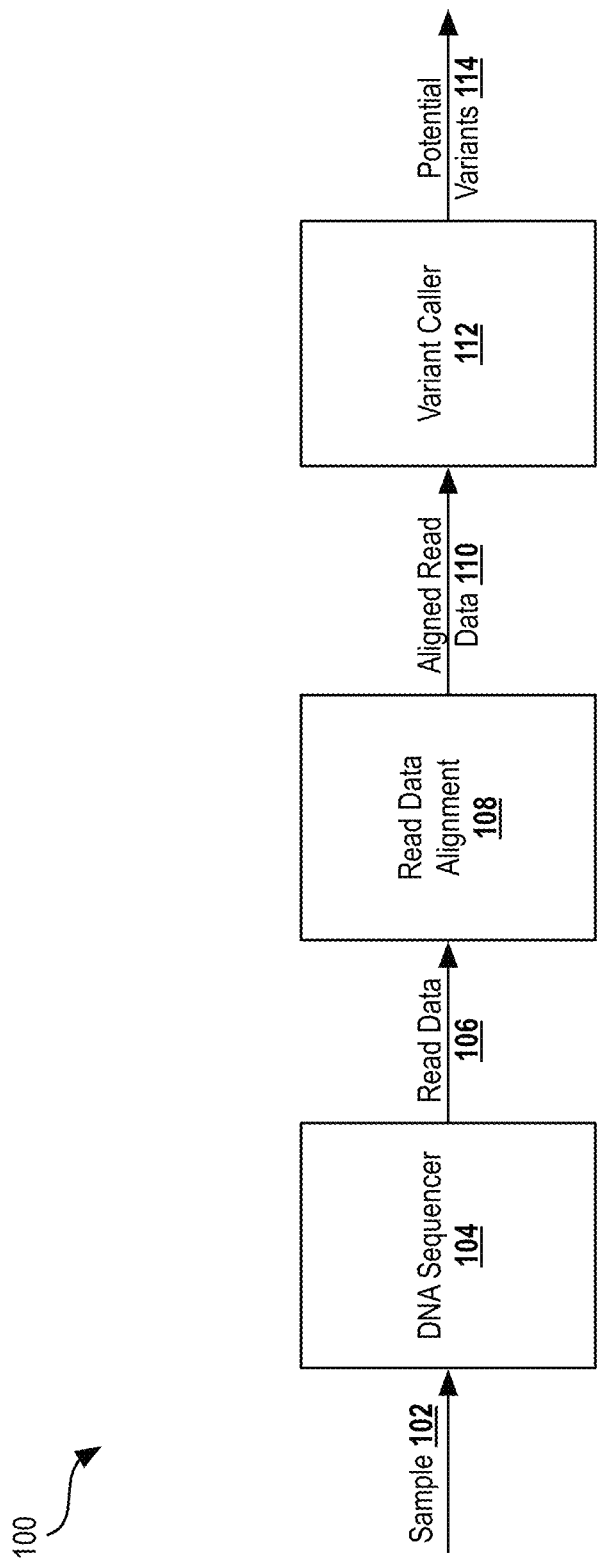
FIG. 1 illustrates a block diagram of a DNA sequencing pipeline, according to an example embodiment.

The following detailed description describes various features and functions of the disclosed systems and methods with reference to the accompanying figures. The illustrative system and method embodiments described herein are not meant to be limiting. It may be readily understood that certain aspects of the disclosed systems and methods can be arranged and combined in a wide variety of different configurations, all of which are contemplated herein.

I. INTRODUCTION

Next generation sequencing (NGS) has dramatically reduced the time and cost required to sequence an entire genome. Previous techniques involved sequentially reading out DNA fragments and having trained biochemists arrange the read data to determine the sequence of entire chromosomes. NGS technologies substantially parallelize the sequencing process, allowing millions of DNA fragments to be read simultaneously. Automated computational analyses then attempt to align the read data to determine the nucleotide sequence of a gene locus, gene, chromosome, or entire genome.

The increasing prevalence of NGS technologies have generated a substantial amount of genome data. Analysis of this genome data—both for an individual sample and for multiple samples—can provide meaningful insights about the genetics of a sample or species. Variations between genomes may correspond to different traits or diseases within a species. Variations may take the form of single nucleotide polymorphisms (SNPs), insertions and deletions (INDELs), and structural differences in the DNA itself such as copy number variants (CNVs) and chromosomal rearrangements. By studying these variations, scientists and researchers can better understand differences within a species, the causes of certain diseases, and can provide better clinical diagnoses and personalized medicine for patients.

The quality and accuracy of genome datasets is crucial to all subsequent analyses and research performed on those datasets. However, NGS technologies used to generate these genome datasets are imperfect, and sources of error in both the read process itself and the read data alignment can lead to uncertainty. If an NGS machine incorrectly reads a nucleobase and records it in the read data, subsequent analysis could incorrectly identify a variant at that locus. If there are inaccuracies in the alignment of the read data, incorrect variant detection might also occur. If these sources of error are left unaccounted for, false positive variant detection could lead to incorrect clinical diagnoses or the discovery of non-existent variants.

To mitigate these errors, some NGS analysis pipelines include filtering steps to detect and discard of false positive variant detections. Herein, a variant detection may be referred to as a "variant call." Some filtering techniques utilize hard filters that analyze one or more aspects of a variant call, compare it against one or more criteria, and provide a decision as to whether it is a true positive variant call or a false positive variant call. For example, if multiple read fragments aligned at a particular locus show three or more different bases, a hard filter might determine that the variant call is a false positive.

Other filtering techniques employ statistical or probabilistic models, and may involve performing statistical inferences based on one or more hand-selected variables of the variant call. A variant call might include a set of read data of DNA fragments aligned with respect to each other. Each DNA fragment read data may include metadata that specifies a confidence level of the accuracy of the read (i.e., the quality of the bases), information about the process used to read the DNA fragments, and other information. DNA sequencing experts may choose features of a variant call that they believe to differentiate true positives from false positives. Then, a statistical model (e.g., a Bayesian mixture model) may be trained using a set of labeled examples (e.g., known true variant calls and the quantitative values of the hand-selected features). Once trained, new variant calls may be provided to the statistical model, which can determine a confidence level indicative of how likely the variant call is a false positive.

One approach involving such statistical model filtering involves a set of five steps: (1) initial read alignment; (2) local realignment around INDELs; (3) base quality score recalibration; (4) SNP discovery and genotyping to find all potential variants; and (5) applying the statistical model to separate true variants from false variants produced by machine artifacts. See Depristo, M. A. et al. (2001) A framework for variation discovery and genotyping using next-generation DNA sequencing data. Nat. Genet. 43, 491-498.

The effectiveness of false positive filtering using statistical models is limited by features chosen by the designer of an NGS analysis pipeline. This deficiency is likely a result of an inadequate representation of the true sources of variation by the handcrafted features. However, the features that distinguish true positive from false positives, and the relative importance of each of those features, is generally not known prior to training. Thus, improving the accuracy of such a statistical model may involve manually assessing this filtering, examining the outputs, and selecting different features and/or tuning the weighting of each of these features in the statistical analysis. In some circumstances, a variant call may include dozens or hundreds of read fragments (of varying lengths), each of which could include dozens or hundreds of nucleotides. Thus, the number of permutations of a variant call is incredibly large. Accordingly, it would be impractical or nearly impossible for a human to analyze the effectiveness of each possible feature of a variant call.

False positive variant calls may be avoided or mitigated by performing more accurate read sequence alignment, and/or by improving the robustness of the variant callers themselves. Some variant callers may detect SNPs and INDELs via local de-novo assembly of haplotypes. When these variant caller encounters a read pileup region indicative of a variant, the variant caller may attempt to reassemble or realign the sequence reads. By analyzing these realignments, these types of variant callers may evaluate the likelihood that the read pileup region contains a variant.

In some instances, these de-novo variant callers carry out steps of (1) defining the read pileup region, (2) realigning the sequence reads within that read pileup region, and (3) using a statistical model (e.g., a Hidden Markov Model) to evaluate the likelihood that a variant exists in within the read pileup region. While de-novo variant callers (e.g., HalpotypeCaller of the genome analysis toolkit (GATK)) can detect most SNPs and INDELs from sequence read data, the models upon which they rely utilize handcrafted features to assess whether a particular region contains a variant. Even with expert intervention, such handcrafted features produce statistical models that have limited robustness.

Analysis pipelines, techniques, and methods disclosed herein involve using deep learning to autonomously extract features from variant call data, and train models to characterize errors in the sequencing process (including read processes, sequence read alignment, and variant calling). Rather than building statistical models based on handcrafted features, techniques of the present disclosure involve training neural networks to extract features from DNA sequencing data. Using a reference data set of a whole genome, stages of an NGS analysis pipeline may be modeled, such that the contours of the models represent errors at each of the stages.

An example analysis pipeline includes an alignment stage that receives read sequencing data representing a number of nucleotide sequence fragments and aligns them with respect to each other and a reference genome sequence. An alignment operation might attempt to place a sequence read fragment at a particular location within a gene locus (e.g., based on the sequence read nucleotides matching or approximately matching the reference genome at that location). The alignment operation might also assign a score or confidence level indicating a likelihood that the sequence read is positioned correctly within the genome. Using a reference data set containing a set of sequence reads and a known genome sequence (e.g., a well-characterized reference genome that has been independently verified and considered accurate to within a statistical certainty), each alignment can be labeled as either correct or incorrect. By providing these sequence read alignments to a deep learning tool, features may be extracted that distinguish correct alignments from incorrect alignments.

An example analysis pipeline might also include a variant calling stage that receives aligned sequence reads and identifies potential variants from among those aligned sequence reads. A variant caller might, as one example, determine whether or not a particular nucleotide position contains a heterozygous SNP based on that particular nucleotide position having overlapping sequence reads of two or more different nucleotide bases. By evaluating or quantifying features of a read pileup window that encompasses the potential variant, the variant caller might generate a confidence level indicating the likelihood that the evaluated nucleotide position contains a variant. Using a set of read pileup windows based on aligned read data from a reference genome and a known genome sequence, each read pileup window may be assigned a label of a variant or a non-variant (i.e., a "reference"). Providing these read pileup windows and labels to a deep learning tool, such as a neural network, may train the network and identify features that distinguish read pileup windows including variants from read pileup windows without variants.

Further, an example analysis pipeline might also include one or more filtering stages that distinguish false positive variant calls (i.e., variant calls identified by the variant caller that are not known variants in the reference genome) from true positive variant calls. More specifically, a filtering stage might include a neural network trained to characterize read pileup windows and extract features that distinguish false positives from true positives.

A DNA sequencing analysis pipeline incorporating neural networks at various stages of the pipeline may improve accuracy of alignment, variant calling, and false positive variant filtering, among other aspects of the pipeline. The features encoded within the trained neural networks may generally model the errors of various processes, tools, or algorithms in the pipeline, and provide more accurate likelihoods and confidence levels compared to hand-crafted machine learning tools.

Many different read processes may be used to generate DNA fragment read data of a sample. Each read process may vary by read length, amplification method, materials used, and the technique used (e.g., chain termination, ligation, etc.). The nature and source of the errors of each read process may vary. Thus, the features that distinguish incorrect alignments, invalid variant calls, or false positive variant detections may differ among read processes. Accordingly, the above-described deep learning techniques may be applied to multiple different read processes to develop a library of classifiers or models. In this manner, an NGS analysis pipeline may be capable of accurately detecting incorrect alignments, invalid variant calls, or false positive variant detections from read data generated by a variety of read processes.

A classifier trained in the manner described above may receive as input sequencing data, and may subsequently output a set of probabilities or confidence values indicating a likelihood that an alignment, variant call, or variant detection is accurate. Subsequent analyses may be carried out based on these probability or confidence value outputs. As one example, if a particular alignment is determined to likely be incorrect, a subsequent or parallel stage in the pipeline might attempt to re-align the sequence read to find its correct alignment location. As another example, if a variant call site is determined to likely contain a variant, a subsequent stage might evaluate the likelihood that the initial variant call determination was accurate. In various instances, the confidence value data associated with the reference genome might characterize the read process, sequence read alignment technique, variant calling technique, or some combination thereof. Evaluating the performance of these processes may serve as a basis for improving them. For instance, if the alignment of sequence reads at a location within a particular gene locus is frequently identified to be an incorrect alignment, a developer or analysis pipeline designer might adjust the parameters of the alignment process to allay the common alignment issue. In this manner, the deep learning models might be used to identify software bugs or other problems with an algorithm or technique. An output or report of these errors may be used by NGS sequencer vendors or genetic data analysis toolkit developers to mitigate or eliminate those sources of error.

Some NGS analysis pipelines described herein may include additional stages for further analysis based on the filtered variant calls. In some implementations, a pipeline might evaluate the combination of variant calls to determine the allele of a particular gene. Based on identified alleles, subsequent stages may carry out genotyping or haplotyping to characterize a whole genome. For each of these stages, the input data may be mapped to an image and serve as an input into a neural network trained to identify features that distinguish alleles, genotypes, haplotypes, etc. In some implementations, each of these stages in the pipeline might be instantiated as one or more layers in a single neural network; in other implementations, multiple neural networks may be used to implement the stages in an analysis pipeline.

As the proliferation of NGS technologies continues, the amount of available NGS read data will increase. Trained deep learning models that characterize different stages of an analysis pipeline (or the entire pipeline itself) might be further trained using new data as it becomes available, improving the robustness of those models. Likewise, as more sample genomes are studied and become gold standard reference genomes, labeled variant calls from those new reference genomes may be used to improve the robustness and accuracy of existing classifiers. Thus, an NGS analysis pipeline with background models and classifiers described herein may improve as more training data becomes available.

II. TERMINOLOGY

A. Next Generation Sequencing (NGS)

NGS generally refers to DNA sequencing techniques that involve sequencing multiple DNA fragments of a sample in parallel. The output data may contain nucleotide sequences for each read, which may then be assembled to form longer sequences within a gene, an entire gene, a chromosome, or a whole genome. The specific aspects of a particular NGS technique may vary depending on the sequencing instrument, vendor, and a variety of other factors. Secondary analyses may then involve detecting variants within that sample.

FIG. 1 illustrates a block diagram of a DNA sequencing pipeline 100, according to an example embodiment. The pipeline 100 includes DNA sequencer 104, read data alignment 108, and variant caller 112. As described herein, a "pipeline" may refer to a combination of hardware and/or software that receives an input material or data and generates a model or output data. Pipeline 100 receives a DNA sample 102 as input, which is sequenced by the DNA sequencer 104 and outputs read data 106. The read data alignment 108 then receives the raw input read data 106 and generates aligned read data 110. The variant caller 112 analyzes the aligned read data 110 and outputs potential variants 114.

Sample 102 may be a biological sample (e.g., biopsy material) taken from a particular organism (e.g., a human). The sample 102 may be isolated DNA or RNA, and may contain individual genes, gene clusters, full chromosomes, or entire genomes. The sample 102 may include material or DNA isolated from two or more types of cells within a particular organism.

DNA sequencer 104 may be any scientific instrument that performs DNA sequencing autonomously or semi-autonomously. The DNA sequencer 104 may receive sample 102 as an input, carry out steps to break down and analyze the sample 102, and generate read data 106 containing nucleotide sequences of read fragments. The DNA sequencer 104 may subject DNA from sample 102 to fragmentation and/or ligation to produce a set of DNA fragments. The fragments may then be amplified (e.g., using polymerase chain reaction (PCR)) to produce copies of each DNA fragment. Then, the DNA sequencer 104 may sequence the amplified DNA fragments using, for example, imaging techniques that illuminate the fragments and measure the light reflecting off them to determine the nucleotide sequence of the fragments. Those nucleotide sequence reads may then be output as read data 106 (e.g., a text file with the nucleotide sequence and other metadata) and stored onto a storage medium.

Read data alignment 108 may be any combination of hardware and software that receives raw DNA fragment read data 106 and generates the aligned read data 110. In some embodiments, the read data is aligned to a reference genome (although, one or more nucleotides within a read fragment may differ from the reference genome). In some instances, the DNA sequencer 104 may also align the read fragments and output aligned read data 110.

Aligned read data 110 may be any signal or data indicative of the read data 106 and the manner in which each fragment in the read data 106 is aligned. An example data format of the aligned read data 110 is the SAM format. A SAM file is a tab-delimited text file that includes sequence alignment data and associated metadata. Other data formats may also be used (e.g., pileup format).

Variant caller 112 may be any combination of hardware and software that detects variants in the aligned read data 110 and outputs potential variants 114. The variant caller 112 may identify nucleotide variations among multiple aligned reads at a particular location on a gene (e.g., a heterozygous SNP), identify nucleotide variations between one or more aligned reads at a particular location on a gene and a reference genome (e.g., a homozygous SNP), and/or detect any other type of variation within the aligned read data. The variant caller 112 may output data indicative of the detected variants in a variety of file formats, such as variant call format (VCF) which specifies the location (e.g., chromosome and position) of the variant, the type of variant, and other metadata.

A variant caller 112 may evaluate the aligned read data 110 according to a particular level of sensitivity. In some instances, the variant caller 112 may perform a preliminary assessment of a particular variant to determine the "quality" of that variant. The sensitivity setting of a variant caller 112 may specify a minimum quality level to satisfy the detection of a variant. If the sensitivity setting is low, poor quality variants may be dismissed at this stage as likely false positives. On the other hand, if the sensitivity is high, even poor quality variants may be considered potential variants for subsequent analysis. High sensitivity settings are more likely to capture true variants, while also detecting false positive variant calls.

Potential variants 114 may be any combination of data that is indicative of the detected variants. In some implementations, the potential variants 114 include detected variants and their associated read pileups, along with any other information. The potential variants 114 may include both true positive variant calls (and associated read pileup data) along with false positive variant calls (and associated read pileup data).

B. Reference Genome

As described herein, a "reference genome" may refer to DNA sequencing data and/or an associated predetermined nucleotide sequence for a particular sample. A reference genome may also include information about the sample, such as its biopsy source, gender, species, phenotypic data, and other characterizations. A reference genome may also be referred to as a "gold standard" or "platinum" genome, indicating a high confidence of the accuracy of the determined nucleotide sequence. A reference genome and its associated read data may serve as a basis for training the background model as described in the present disclosure. An example reference genome is the NA12878 sample data and genome. See also Zook, J. M. et al. (2014) Nat. Biotechnol. Vol. 32 No. 3, 245-253.

C. DNA Read Data and Data Formats

DNA read data may be stored in a variety of file formats, such as FASTQ format files, SAM (Sequence Alignment/Map) files, BAM files (binary SAM files), VCF (Variant Call Format) files, and pileup files, among other possible file formats. Each of these file formats may store different information about the DNA read data at various stages within an analysis pipeline.

In some instances, an NGS sequencer may initially output read data in the FASTQ format, which includes nucleotide sequences and associated quality scores (e.g., Phred scores) in an ASCII format (or any other encoding). Then, by comparing the sequence data in the FASTQ file against a reference, a computing device may generate a SAM file that represents aligned read data. In some cases, the SAM file may be compressed and stored as a BAM file. SAM or BAM files may then be provided to a variant caller, which generates VCF files that contain aligned nucleotide sequences along with information about the detected variant. In some instances, the variant data may be stored in the pileup data format.

Each of the data formats may be stored as a text file, binary file, or in another format. For example, some embodiments of the present disclosure map variant data to pixel information (e.g., color, alpha, coordinates, etc.), such that a particular variant read pileup forms an image. Such a transformation from text or binary data to image data may be carried out in a lossless manner, such that the nucleotide bases, quality scores, reference, and other metadata of a read pileup can be extracted from the colors of the pixels and the arrangement of the pixels in the image. In some embodiments, an NGS analysis pipeline might carry out image processing on such image data.

C. DNA Variant Types and Detection

As described herein, a genome may contain multiple chromosomes, each of which may include genes. Each gene may exist at a position on a chromosome referred to as the "gene locus." Differences between genes (i.e., one or more variants at a particular gene locus) in different samples may be referred to as an allele. Collectively, a particular set of alleles in a sample may form the "genotype" of that sample.

Two genes, or, more generally, any nucleotide sequences that differ from each other (in terms of length, nucleotide bases, etc.) may include one or more variants. In some instances, a single sample may contain two different alleles at a particular gene locus; such variants may be referred to as "heterozygous" variants. Heterozygous variants may exist when a sample inherits one allele from one parent and a different allele from another parent; since diploid organisms (e.g., humans) inherit a copy of the same chromosome from each parent, variations likely exist between the two chromosomes. In other instances, a single sample may contain a gene that varies from a reference genome; such variants may be referred to as "homozygous" variants.

Many different types of variants may be present between two different alleles. Single nucleotide polymorphism (SNP) variants exist when two genes have different nucleotide bases at a particular location on the gene. Insertions or deletions (INDELs) exist between two genes when one gene contains a nucleotide sequence, while another gene contains a portion of that nucleotide sequence (with one or more nucleotide bases removed) and/or contains additional nucleotide bases (insertions). Structural differences can exist between two genes as well, such as duplications, inversions, and copy-number variations (CNVs).

Depending on the sensitivity and implementation of a variant caller, read data from a whole genome may include millions of potential variants. Some of these potential variants may be true variants (such as those described above), while others may be false positive detections. A deep learning model for variant calls may identify and weight features that distinguish true variants from false positives.

D. Machine Learning Tools

Machine learning generally refers to a computational technique in which a model is developed for classifying information. A machine learning tool may be trained using training data to classify information according to one or more variables (also referred to as "features"). A model may be trained using supervised learning or unsupervised learning. In supervised learning, a model is trained using labeled examples, where each example is paired with a label indicating the desired classification for that example. In unsupervised learning, a model is trained using unlabeled examples, and the model identifies features and/or classifications based on differences between those examples.

Generally, supervised learning is effective when features that distinguish between two or more classifications is well known. Consider a model that distinguishes between stop signs and yield signs. Features that distinguish between the two types of traffic signs include shape (octagon vs. triangle), color (red vs. yellow, in some cases), and text ("STOP" vs. "YIELD"). In this example, an accurate model can be trained on the basis of these handcrafted features, since the differences between the two types of traffic signs is well known.

However, the effectiveness of supervised learning can diminish when the number of features that distinguish between two classifications increases. For example, yield signs may be red, shaped like a rotated square, and might contain no text or text other than "YIELD" The classifier trained via supervised learning from the features described above might not accurately detect these yield signs that do not strictly adhere to the hand-selected features.

Thus, a classifier trained using supervised learning tends to perform well when the handcrafted features distinguishing two classifications are well understood. Although the classifier might detect a substantial number of yield signs correctly, some images of yield signs with features not considered during supervised training might be incorrectly classified or otherwise not considered to be yield signs.

Likewise, in the context of DNA sequencing and NGS variant detection, the robustness of a classifier trained to distinguish true positive variants calls from false positive variant calls is limited by the extent to which the features considered by the classifier cover all possible differences between true positives and false positives. Unlike traffic signs, the differences between true positive and false positive variant calls can be subtle and complex. A given variant call may include aligned read data in a pileup window (with each read containing a series of nucleotides), quality scores, a reference genome, and other information. Two variant calls can vary in millions of ways (i.e., "parameters"), and the extent to which each parameter impacts the classification between a true positive and a false positive may vary widely. Thus, hand-selecting the relevant features that distinguish true positive variant calls from false positive variant calls may result in an incomplete or inaccurate assessment of those variant calls, potentially leading to incorrect classifications (e.g., identifying false positives that are true variants, or identifying true variants that are false positives).

Furthermore, the features that distinguish true positives variant calls from false positive variant calls may be different for each DNA sequencing read process. Each DNA sequencing read process may involve different chemical processes, read lengths, machines, and alignment techniques. As such, the sources of error (which lead to false positive variant calls) of one read process may differ from those of another read process. Thus, a classifier that considers the same hand-selected features for multiple read processes may be inaccurate, to the extent that those read processes have different sources of error. It would not be feasible for a human to manually assess each read process and hand-select features for each of those read processes. Also, as NGS technologies continue to advance, changes to read processes could change the nature and source of errors.

Unsupervised learning, on the other hand, may be used to extract features from complex data sets. Whereas supervised learning involves training a classifier on the basis of hand-crafted features, unsupervised learning involves the discovery of features that distinguish between two or more classifications. Unsupervised learning can be effective when features of a complex data set are not well known, allowing a machine learning tool to classify an example on the basis of complex patterns involving many features.

Some example deep learning tools and architectures include deep neural networks, convolutional neural networks (CNNs), and belief networks, among other possible architectures. These artificial neural networks may include multiple layers, each of which includes a collection of artificial neurons that may be interconnected in various ways. An example layer may include input nodes that correspond to different sources of input data (e.g., pixel values in an image). Another layer may include a set of interconnected nodes that carry out functions (e.g. rectifier functions, activation functions, etc.) that can provide linear or non-linear pooling to transform a large number of extracted features from the input layer into aggregated feature values. Yet another layer may be a fully-connected classification layer that weights each of the feature values from the pooling layer and outputs a probability value (e.g., a real number between 0 and 1). The specific configuration of each layer and the hyperparameters of the neural network may vary, depending upon the format and type of input data, the number of desired features, and the number of desired output classifications.

Once the features and patterns have been extracted from a data set, those features may serve as a basis for supervised training of other machine learning tools (e.g., classifiers). For a data set containing many variant calls, the unsupervised learning tool might characterize each variant call according to the extracted features. Then, by comparing those characterizations to known classifications of the variant calls, supervising learning can be carried out to generate a classifier.

The supervised training of a classifier may involve determining labels for each variant call of a reference genome. For example, a variant call at a specific position in a gene might contain two or more overlapping reads of different nucleotides, while the reference nucleotide at that position from the reference genome indicates that there is no heterozygous SNP; that variant call may be labeled as a "false positive," since a SNP was detected at a position in the reference genome known to contain only a single nucleotide. Conversely, if the reference genome species a SNP at that reference nucleotide position, the variant call may be labeled as a "true positive," since a known SNP was detected.

III. EXAMPLE VARIANT CALLERS

Variant callers of the present disclosure may utilize deep learning networks to model DNA sequencing processes and sequence read alignment processes. These deep learning models may extract features of these processes that distinguish true variants in gene sequencing data from false variants or reference nucleotides. The following subsections describe an example set sub-stages in a variant caller.

Figure 2:
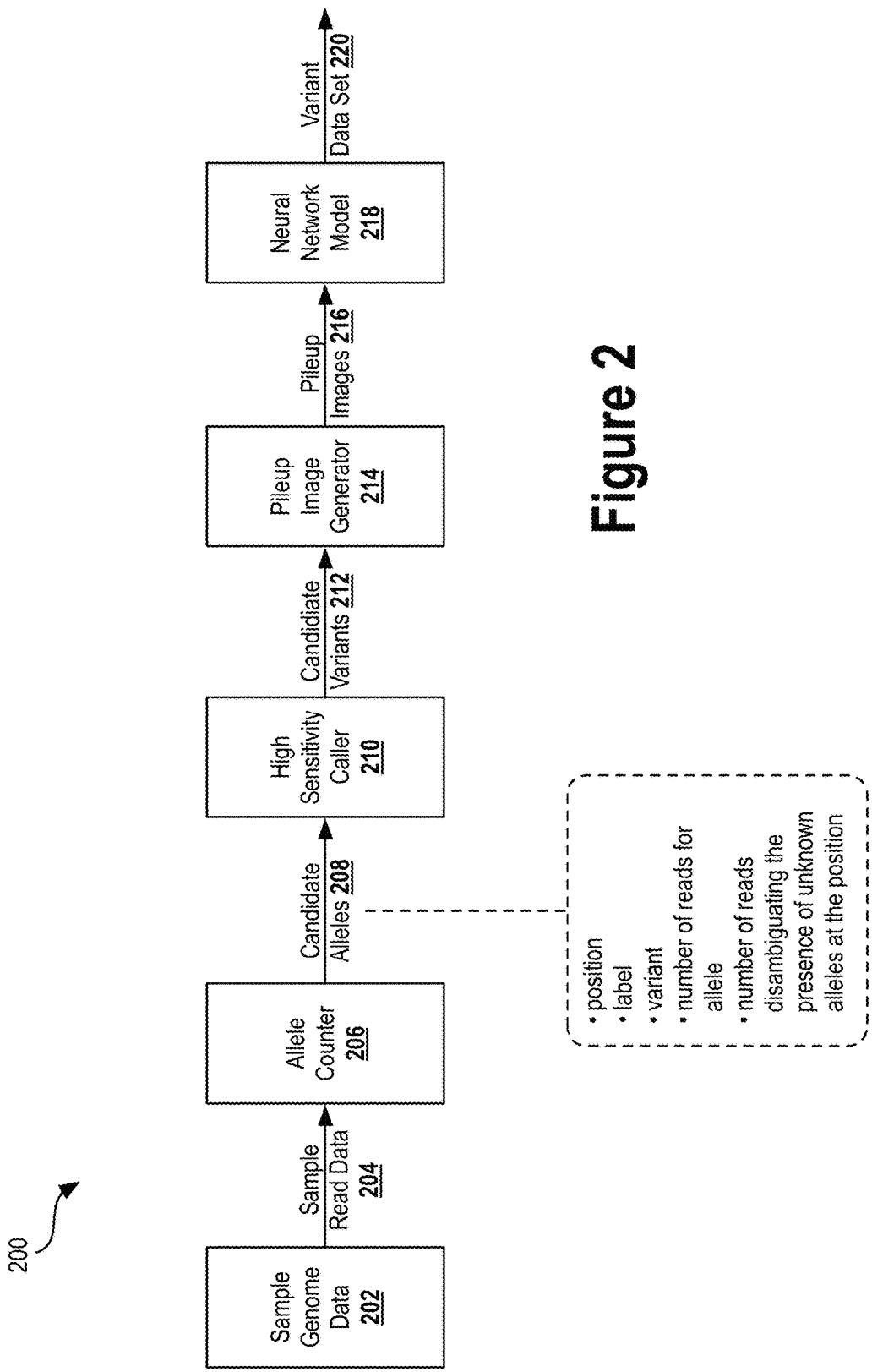
FIG. 2 illustrates an example pipeline of a variant caller, according to an example embodiment.

FIG. 2 illustrates an example pipeline 200 of a variant caller, according to an example embodiment. The variant caller pipeline 200 begins with sample genome data 202. The sample genome data 200 includes sample read data 204, which includes a set of sequence reads (e.g., data representing nucleotide sequences of DNA fragments from a DNA sequencer). Each sequence read and/or nucleotide base may include an associated confidence score. The sample read data 204 may be provided as input to the allele counter 206. The pipeline 200 generally involves evaluating read pileup windows (containing overlapping sequence reads aligned at a particular location within the genome) against known alleles at the respective locations.

The sample genome data 202 may include any combination of data that represents DNA read fragments, the alignment of those read fragments, a nucleotide sequence of the genome, and any other metadata for a particular sample. As one example, a sample genome 202 may include data output from an NGS sequencer that sequenced a sample from an individual. In some instances, the sample genome data 202 may include read data generated using a single read process, such that subsequent stages in the pipeline characterize errors from that single read process. In other instances, the sample genome data 202 may include read data generated from multiple different read processes, such that multiple models may be produced corresponding to each read process.

A. Identifying Candidate Alleles

A given position in the human genome may be associated with one or more known alleles, each of which having its own unique nucleotide sequence within a chromosome. The allele counter 206 may receive the sample read data 204 and determine, for each nucleotide position in the sample read data 204, candidate alleles that might be present at those nucleotide positions. In one implementation, if the allele counter 206 determines that the nucleotide bases of three or more sequence reads agree with a particular allele (e.g., a known allele at that position in the human genome), the allele counter 206 may decide that the particular allele is a candidate allele. Note that two or more candidate alleles may be identified for a particular nucleotide position in the genome.

Each allele candidate may include information used in subsequent analyses to determine candidate variants, to generate pileup images, and/or to score the variant determinations. For example, a candidate allele may include information about the allele's position in the genome, a label describing the allele, the type of variant identified, the number of reads from the sample read data 204 used to identify that allele, and/or the number of reads from the sample read data 204 disambiguating the presence of unknown alleles at the position of the allele.

B. Identifying Candidate Variants

Then, for each candidate allele in the candidate alleles 208, the high sensitivity caller 210 may independently and in parallel select candidate sites of mutation by calling alleles with a highly permissive threshold. These "calls" manifest by appending information into data objects that represent the candidate alleles 208 and contain information about the potential variants. This substage may output, for downstream analyses, candidate variants 212 (i.e., explicit variant records) for deep learning genotyping at all haplotype reference consortium sites. This output may serve to improve sequence alignment, variant calling, and variant filtering models.

The information contained within the candidate variants 212 may serve as the basis for subsequent data process and analysis. These candidate variants 212 may be provided to pipelines that include deep learning via read pileup images, an assembly pipeline, and/or a copy number variation detection algorithm. This "snapshot" of the analysis data at this stage in the pipeline may be useful for improving the pipeline itself as well.

Note that, as described herein, a "candidate allele" or "candidate variant" may refer to a data object that contains information about the sample read data, identified alleles, variant types, and any other information determined in the pipeline 200. The data object may also be referred to as a "proto." As the proto moves through the pipeline, information within the proto may be removed, added, or modified.

C. Creating Pileup Images

Then, for each candidate variant of the candidate variants 212, the pileup image generator 214 may independently extract all overlapping reads from the original read data set and construct an image that represents the candidate variant and associated read data (i.e., a read pileup window that includes reads aligned with the candidate variant). Pixel location and color channels may serve to represent values stored within the proto. Mapping proto data to pixel location and pixel color values within an image may provide a neural network with training data from which patterns can be identified. The pileup image generator 214 may render a set of pileup images 216 and output them to the neural network model 218.

D. Applying the Pileup Images to a Neural Network Model

For each read pileup image, a trained neural network model 218 may be used to determine a probability distribution over the possible genotype configurations as a probability that the candidate variant site is a true mutation (rather than a false positive detection). The output from this substage may be, in some instances, new proto objects that store therein information about the quality of the analysis and the genotype likelihoods. This information may be collectively output as a variant data set, and may include any combination of information obtained or generated within the pipeline 200.

The variant data set 220 may, in some instances, be stored on a computer readable medium for later processing or analysis. The variant data set may aid in certain clinical diagnoses or genetic analyses of a patient, or be used for research or other purposes (depending upon privacy decisions of the individual whose genome was analyzed).

In some embodiments, the variant data set 220 may provide a basis for iteratively realigning the read sequences to improve the accuracy of the determined genome. If a particular variant is correctly detected (to within a statistical certainty), any aligned sequence read that disagrees with the variant may be realigned to conform with the variant. This iterative realignment may not only serve to improve the quality of the variant calls, but may also be used to identify sources of error in a read process or in the technique used to initially align the read sequences.

E. Labeling and Reassembling Ambiguous Regions

Figure 3:
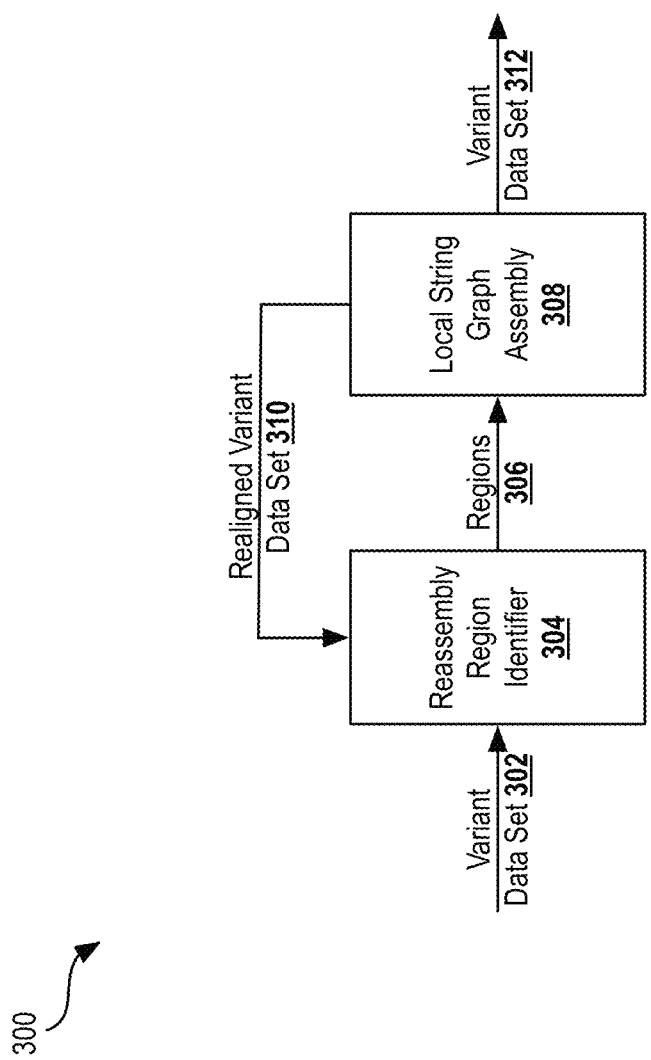
FIG. 3 illustrates a realignment pipeline to carry out iterative realignment, according to an example embodiment.

As described above, the variant data set 220 may be used to iteratively realign sequence reads. FIG. 3 illustrates a realignment pipeline 300 to carry out iterative realignment, according to an example embodiment. In this example, a variant data set 302—which may be similar to or the same as variant data set 220—may be provided as input to the reassembly region identifier 304.

For each variant in the variant data set 302 (which contains quality values and genotype likelihoods), read pileup regions containing ambiguity (determined based on model-derived confidences) may be identified by the reassembly region identifier 304. Identified regions of ambiguity may be passed through subsequent processing to clean up those ambiguous regions using local assembly (i.e., on a small fraction of the whole genome). Cleaning up the ambiguous regions may improve the alignment confidence or the accuracy of allele determination. The reassembly region identifier 304 may mark or label the regions (e.g., read pileup windows) that exhibit some extent of ambiguity, such that some of the sequence reads in those regions may be misaligned. The reassembly region identifier may output identified regions 306 to the local string graph assembly 308.

F. Iterative Local Reassembly

The local string graph assembly 308 may, for each region in regions 306, independently gather all of the overlapping read sequences and carry out a reassembly procedure to determine likely haplotypes from the read data. The variant caller may then realign each read to the determined likely haplotypes. This substage may further improve the accuracy of the alignment.

In some embodiments, the local string graph assembly 308 may output a realigned variant data set 310 back to the reassembly region identifier 304, to reevaluate the variant data set. The reassembly region identifier 304 may repeat the marking or labelling of any ambiguous regions in the realigned variant data set 310. If any ambiguous regions are identified from the realigned variant data set 310, data of those regions may be output to the local string graph assembly 308. The process of reassembly may then be repeated for any outstanding ambiguous regions. This iterative process of evaluation and assembly may be repeated any number of times to reduce the number of ambiguous regions and improve the accuracy or confidence of the identified variants.

G. Exporting the Data

The data generated by the realignment pipeline 300 may then be output and stored on a computer readable medium or other device. In some implementations, a VCF (or a derivative file format thereof) may be used to encode variant calling information into a data file. The file may include all discovered mutations in the sample, along with confidence levels for every nucleotide base in the sample's genome (for subsequent genomics analyses). The data output by the realignment pipeline 300 may be the variant data set 312. Collectively, the stages of a variant caller pipeline 300 described above may serve to classify genetic mutations and evaluate the genetic makeup, mutations, alleles, and haplotypes of a particular DNA sample.

H. Training Variant Caller Models

Generating a classifier or model for various stages in the pipeline 200 and/or pipeline 300 may involve a combination of unsupervised learning and supervised learning. Initially, training a deep learning network with training data from a reference genome produces a background model that has encoded therein features that distinguish those training data examples (e.g., read pileup windows) from each other. A reference genome may include a known sequence of nucleotides, such that labels for candidate alleles, candidate variants, pileup images, and/or identified regions may be determined (e.g., whether a variant is a true positive or false positive, whether a sequence read is correctly aligned, whether a candidate allele exists in the genome, whether a candidate variant is correctly identified, etc.). Using these labels, the classifications discovered by the deep learning network may be characterized via supervised learning.

Deep learning networks may be used to implement the allele counter 206, high sensitivity caller 210, neural network model 218, reassembly region identifier 304, and/or the local string graph assembly 308. In some embodiments, a deep learning network may encompass two or more stages, where a given stage may be associated with one or more layers within the deep learning network. In other embodiments, separate deep learning networks may be implemented for each of the stages.

In some implementations, a deep learning network includes a number of layers, including an input layer, one or more "hidden" layers, and a classification layer. The input layer may sample a variant call (e.g., an image representation of a variant call read pileup window). Each hidden layer may be a pooling layer, a rectified linear unit (ReLU) layer, a fully connected layer, or a down-sampling layer. The classification layer (i.e., the regression layer) may then weight each of the feature values determined in the hidden layers to generate one or more output layers.

Data representative of a variant call may be a read pileup window that encompasses the potential variant. A "read pileup window" may refer to aligned read data spanning across a number of base pairs. As an example, if the potential variant is a SNP at a particular position in a gene, the read pileup window may include any DNA fragment read data (or portion of a DNA fragment read data) that aligns with a reference genome sequence within a range of positions before or after the SNP location (e.g., a window spanning 20 nucleotide positions in a gene including the detected SNP). In some implementations, the read pileup information at a candidate variant site may be mapped to pixel colors and locations to form an image.

In some implementations, the training data used to train a deep learning network and/or classifier includes read pileup windows (or images representing read pileup windows) for each nucleotide position in the entire genome. For a reference genome where each variant site is known, each read pileup window may be labeled as either a "variant" or a "reference" (i.e., non-variant). Training a deep learning network may involve providing each of the read pileup windows—including both known variants and non-variants—to the deep learning network. Then, the classifier or classification layer of a deep learning network may be trained using the "variant" or "reference" labels for each of those read pileup windows.

Note that the variant data sets 220 and 312 are associated with a particular read process (specifically, the read process used to generate the sample genome data 202). Thus, trained models may be applied to read pileup windows from read data generated using that same read process. If a different read process is employed (e.g., a different NGS sequencer, a different fragment base pair length, different amplification method, etc.), the trained models may not accurately evaluate the feature values of data generated using that different read process.

IV. EXAMPLE VARIANT CALL PIPELINE

Figure 4:
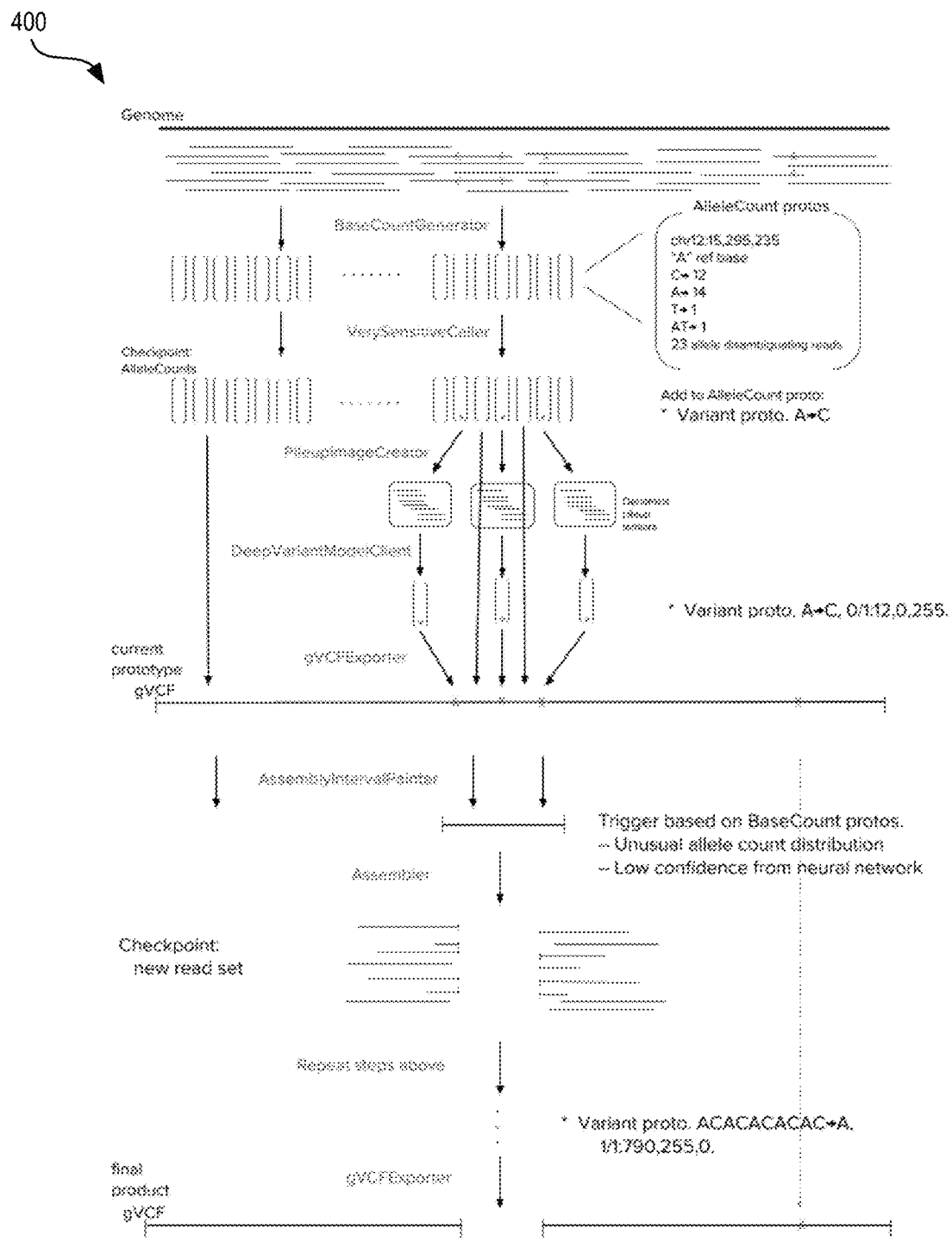
FIG. 4 is a conceptual diagram illustrating a flow of an example pipeline 400, according to an example embodiment (SEQ ID NO:01).

FIG. 4 is a conceptual diagram illustrating a flow of an example pipeline 400, according to an example embodiment. The example pipeline 400 may be similar to or the same as pipeline 200 in FIG. 2 and/or pipeline 300 in FIG. 3. In example pipeline 400, genome data may be provided to a "BaseCountGenerator," which may be similar to or the same as the allele counter 206; the "VerySensitiveCaller" may be similar to or the same as the high sensitivity caller 210; the "PileupImageCreater" may be similar to or the same as the pileup image generator 214; and the "DeepVariantModelClient" may be similar to or the same as the trained neural network model 218. Each of the stages may be performed in parallel for multiple nucleotide positions in the genome. Collectively, the "DeepVariantModelClient" may output information representing potential variant calls for multiple locations in the genome.

Additionally, the example pipeline 400 includes an "AssemblyIntervalPainter," which may be similar to or the same as the reassembly region identifier 304, and the "Assembler" may be similar to or the same as the local string graph assembly 308. The "Assembler" may output a set of variant calls and associated metadata in the gVCF file format.

V. EXAMPLE DEEP LEARNING NETWORKS

Figure 5:
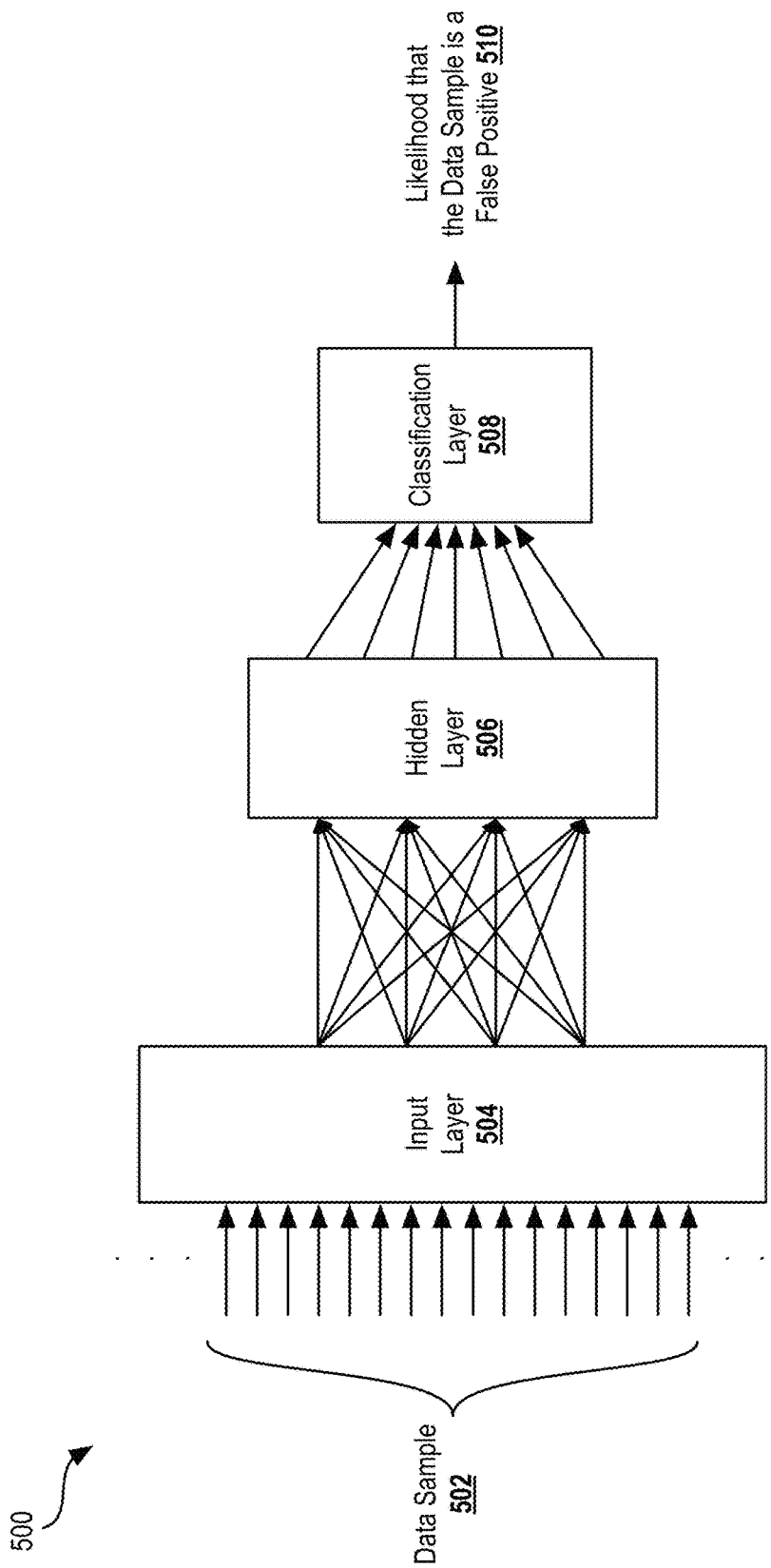
FIG. 5 illustrates a block diagram of a neural network, according to an example embodiment.

FIG. 5 illustrates a block diagram of a neural network 500, according to an example embodiment. The neural network includes an input layer 504, a hidden layer 506, and a classification layer 508. The input layer 504 receives data sample 502 as input, which is decomposed and passed along to the hidden layer 506. Nodes of the hidden layer 506 may form connections with nodes in the classification layer 508. The classification layer 508 may then weight the feature value determinations from the hidden layer and map it to an output value representing the likelihood 510 that the data sample 502 is a false positive. Generally, a "false positive" may also be a confidence level indicating the likelihood that the data sample 502 is a particular classification (e.g., a particular allele, a particular variant type, etc.)

In some embodiments, the data sample 502 may be an image representing a read pileup window that at least partially encompasses a potential variant. As one specific example, the image could be a 40×200 pixel image (representing a window that is 200 nucleotide positions wide and covering up to 40 different overlapping read fragments) with 3 color channels (e.g., red, green, and blue). Each pixel in the image may be mapped to information about a specific nucleotide at particular position aligned at a reference position with respect to a reference genome. One color channel might represent whether the nucleotide base is an A, C, G, or T. Another color channel might represent the "quality" score of that nucleotide read. Yet another color channel might be mapped to whether or not a read strand nucleotide exists at that location. Additionally, the transparency of the color channels with respect to a reference color (e.g., black) might indicate whether or not that pixel matches the reference genome (e.g., where fully transparent represents a mismatch, and fully opaque represents a match).

The data sample 502 image may be provided to the input layer 504. More specifically, the pixels of data sample 502 may be mapped input channels of the input layer 504.

The hidden layer 504 may include any combination of nodes and connections that collectively form a network. In some embodiments, the hidden layer 504 is a ReLU activation layer containing 15×15 nodes. The hidden layer may apply an elementwise activation function (e.g., a maximum function thresholding at zero).

The classification layer 506 may be a fully-connected layer that computes a score representing the likelihood that the input image represents a false positive variant read pileup window. In some embodiments, the classification layer 506 may be a logistic regression layer with 15×1 nodes and outputs a real number between 0 and 1.

In other implementations, additional layers may be included within the neural network 500. For example, the neural network 500 may include any number of convolutional layers, additional down-sampling or pooling layers, and/or other types of layers.

VI. EXAMPLE MODEL OUTPUTS

Figure 6:
FIG. 6 is a table illustrating an output of a model, according to an example embodiment.

FIG. 6 is a table 600 illustrating an output of a model or variant caller, according to an example embodiment. The table 600 may illustrate, for example, the output from the trained model 316, the output from the variant data set 312, and/or the output of neural network 500.

In an example analysis pipeline, a set of variant calls may be provided to a trained model to determine the likelihoods that those variant calls are false positives. Each variant call will have an associated "score" indicative of this likelihood. Table 600 illustrates this relationship between variant calls and likelihood scores. In this example, a likelihood of 1 indicates a 100% confidence level that the variant call is a false positive, whereas a likelihood of 0 indicates a 0% confidence level that the variant call is a false positive (in other words, a true positive). Note that, in other instances, the range of values that a score may take on may depend on the manner in which a trained classifier or classification layer is implemented.

In various embodiments, a subsequent analysis may be performed to determine whether or not each variant call is a false positive (i.e., a binary interpretation, rather than a confidence value). In some instances, a threshold level of confidence may be designated to indicate that the variant call is a false positive (e.g., likelihoods greater than 0.9 could be considered false positive, depending on the particular implementation). This threshold level of confidence may be selected manually, or might be determined on the basis of data. For instance, once the neural network and classifier are trained (i.e., both unsupervised and supervised learning has been completed), the training data may be provided to the classifier again to generate likelihood scores for each of the potential variants. Since the training data is labeled, each potential variant is known to be a true positive or a false positive. In some embodiments, the likelihood threshold might be set to the lowest likelihood output from the subset of the training data containing known false positives (i.e., the likelihood score associated with the known false positive example closest to the boundary between false positives and true positives).

The likelihoods may be output in a data format and/or provided to a computing device or storage medium. The likelihoods may also be graphically displayed to illustrate relationships between the likelihoods and one or more feature values, such as the feature values extracted from the neural network. The likelihoods may also be provided as inputs into subsequent analyses in which potential variants with high likelihood scores are discarded or otherwise labeled as false positives. In some contexts, such as personal genomics and clinical diagnoses, the likelihoods could be used to indicate a level of certainty that a particular patient has a certain trait or is afflicted with a particular genetic disease; this information could further provide a basis for evaluating medical treatment options or whether to perform certain diagnostic testing (e.g., if a certain variant is linked to a particular medical condition, a very low likelihood of the variant being a false positive might inform a doctor or patient to conduct further testing or diagnoses for verification).

Additionally, the variant call-likelihood pairs could serve as a basis for identifying sources of error in a particular NGS sequencer or analysis pipeline. If, for a particular read process, a specific variant call site is frequently associated with a high likelihood of being a false positive, then the false positive detection data could help pinpoint the source of error. By mining the variant call and likelihood data to identify sources of error, the accuracy and reliability NGS sequencers and analyses pipelines could be improved.

VII. EXAMPLE VARIANT CALL READ PILEUP WINDOWS

Figure 7A:
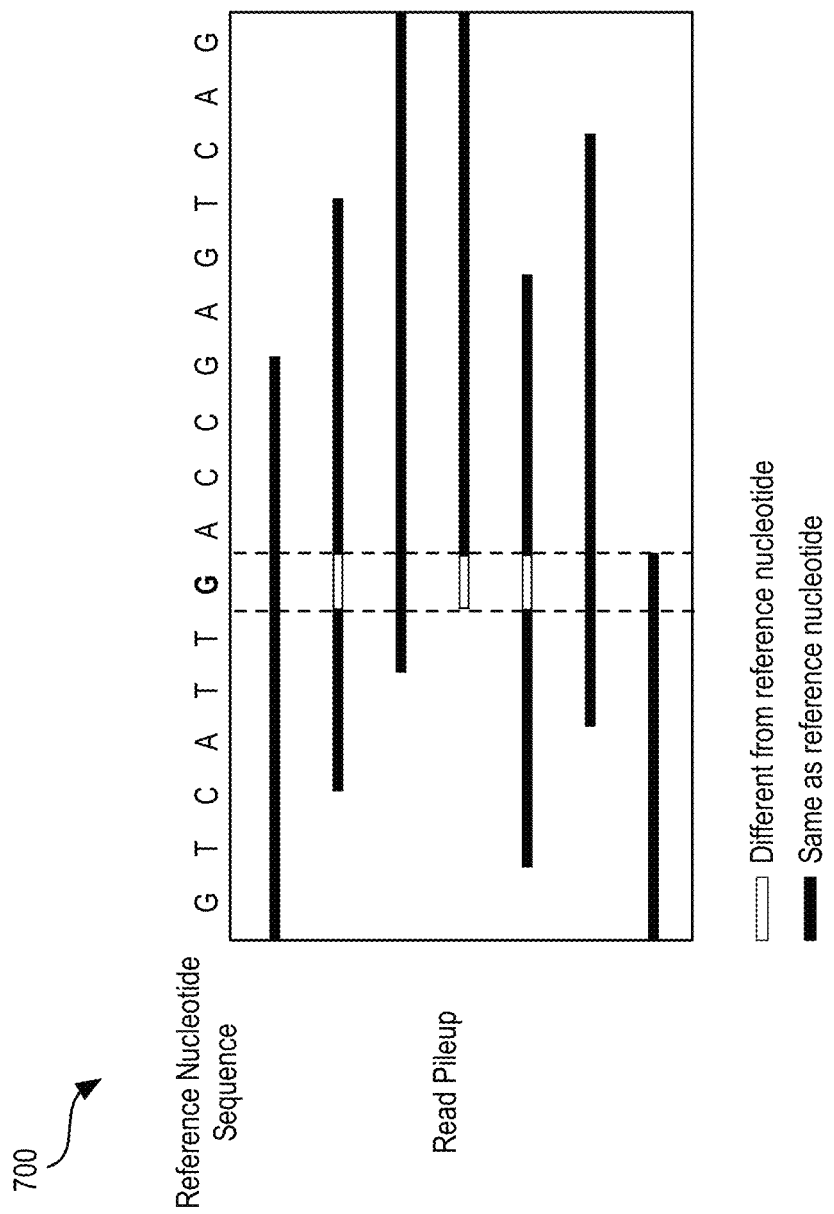
FIG. 7A illustrates a variant call read pileup window, according to an example embodiment (SEQ ID NO:02).

FIG. 7A illustrates a variant call read pileup window 700, according to an example embodiment. In this example, the read pileup window includes seven read fragments that overlap at a particular nucleotide location (denoted by the dotted lines). The pileup window spans across seventeen nucleotide bases. In FIG. 7A, a read fragment that is colored black indicates that the nucleotide at that position is the same as the nucleotide in the associated reference nucleotide sequence (that is, the nucleotide base in the reference genome vertically aligned with that nucleotide). A read fragment that is colored white indicates that the nucleotide at that position is different from the nucleotide in the associated reference nucleotide sequence.

In this example, the second, fourth, and fifth read fragments (counting from the top down) have a different nucleotide than the associated nucleotide base in the reference genome. Depending on the variant caller, this read pileup window might be detected to be a SNP variant.

Figure 7B:
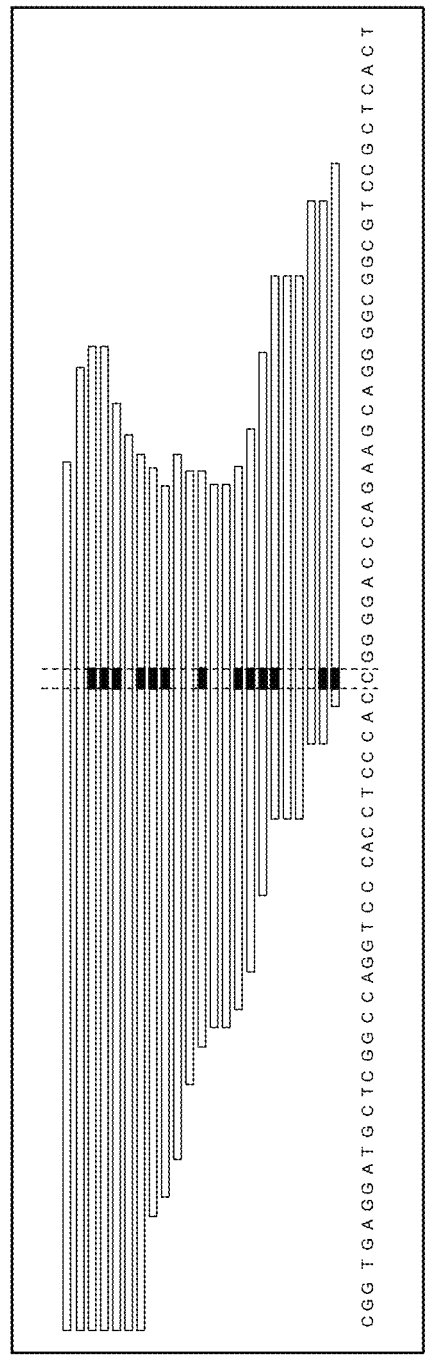
FIG. 7B illustrates a variant call read pileup window, according to an example embodiment (SEQ ID NO:03).

FIG. 7B illustrates a variant call read pileup window 750, according to an example embodiment. The read pileup window 750 illustrated in FIG. 7B may be an example read pileup window similar to that depicted in FIG. 7A.

VIII. EXAMPLE IMAGE REPRESENTATIONS OF VARIANT CALLS

Figure 8A:
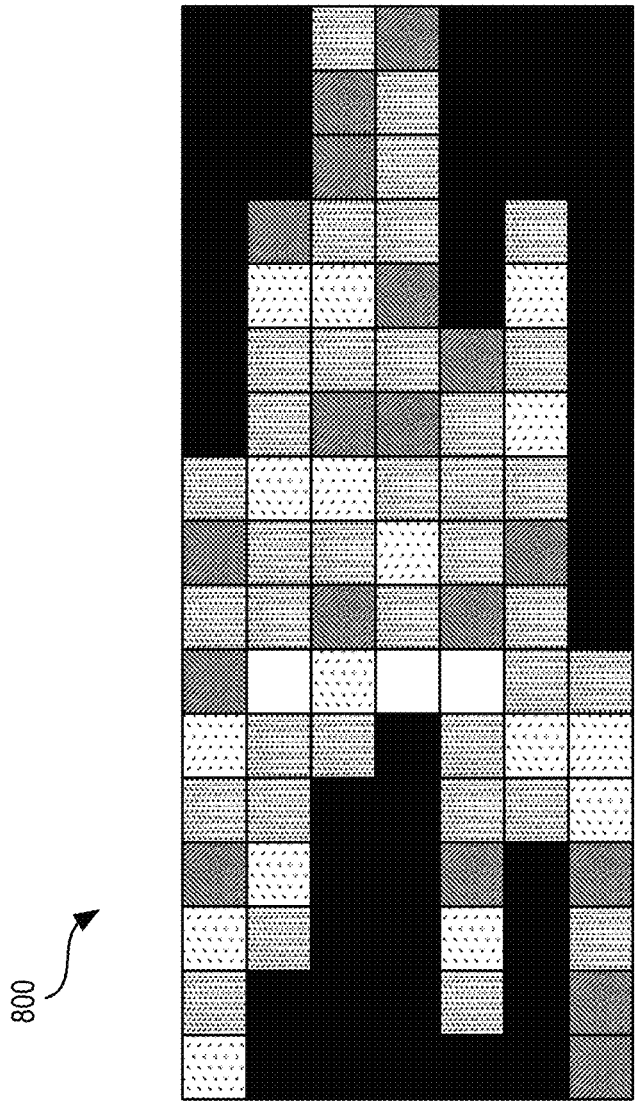
FIG. 8A illustrates an image representation of a variant call, according to an example embodiment.

FIG. 8A illustrates an image representation 800 of a variant call, according to an example embodiment. The image 800 in FIG. 8A represents the read pileup window 700 in FIG. 7A. Each pixel includes a horizontal position (a nucleotide position on the read fragment aligned with the reference genome) and a vertical position (the particular read fragment). In this example, black pixels indicate a lack of read fragment data at that position, while shaded pixels indicate the presence of a read fragment at that position. The extent of shading represents a combination of information (e.g., the nucleotide base, whether or not the base matches the reference genome, the quality score, etc.). If no shading is present in a pixel, the nucleotide base at that location differs from the nucleotide at that location in the reference genome.

Based on the shading (and, in other implementations, color), image analysis and pattern recognition performed by a neural network may identify patterns in the image. For example, the three non-shaded (white) squares in the image 800 represent a disagreement with the associated reference nucleotide. A neural network trained using a data set containing many example images (such as image 800) may detect features in the shading or color of the images that are indicative of false positives variants or true positive variants. Errors in the DNA sequencing process that lead to false positive detection may be graphically embodied in the images that represent read pileup windows; a neural network may be trained to identify these aberrations, colors, or other patterns in the images (generally, "features"). Once these graphical features have been identified, training a classifier or classification layer using labels for those images may generate a model capable to determining the likelihood of a read pileup window representing a false positive variant call based on characteristics and features of an image representation of that read pileup window.

Figure 8B:
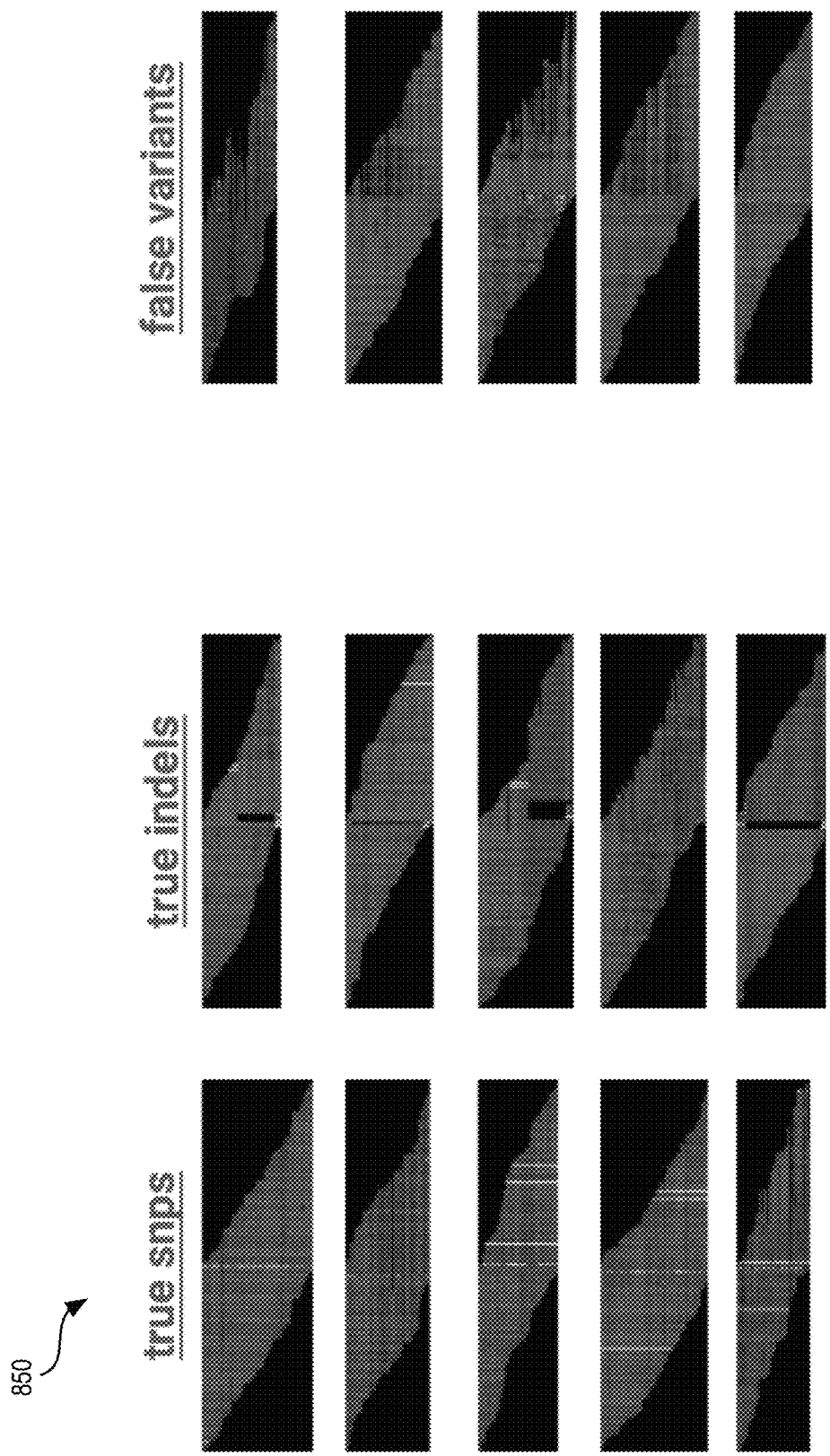
FIG. 8B illustrates image representations of variant calls, according to an example embodiment.

FIG. 8B illustrates example image representations 850 of variant calls, according to an example embodiment. In FIG. 8B, images labeled "true snps" represent read pileup windows that include SNPs, images labeled "true indels" represent read pileup windows that include insertions or deletions, and images labeled "false variants" represent read pileup windows of false positive variant calls. Note that FIG. 8B are example images similar to the image 800 depicted in FIG. 8A.

As shown in the image representations 850, the read pileup windows of true SNPs include distinct bright vertical lines. The read pileup windows of true INDELs include large dark gaps spanning large sections of the read pileup window. The read pileup windows of the false variants include small aberrations and inconsistent gaps (differences between the nucleotide base at that location and the associated reference nucleotide). These example image representations 850 illustrate that a neural network can detect such features as those described above in order to determine (or predict) the likelihood of that a non-labeled read pileup window is a false positive variant call.

IX. PERFORMANCE COMPARISON BETWEEN DEEP LEARNING AND VQSR

Figure 9:
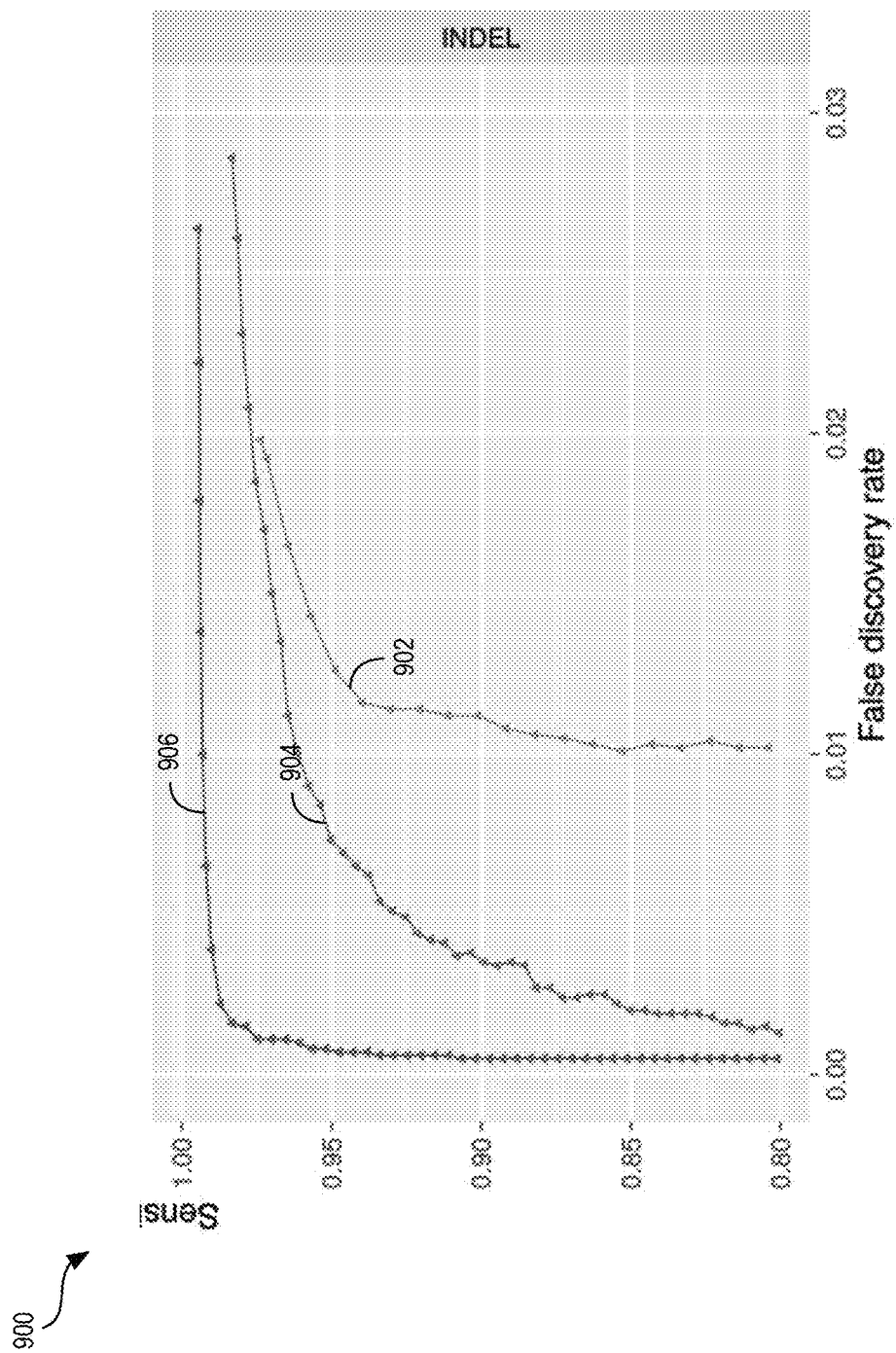
FIG. 9 illustrates a graph comparing the performance of a deep learning model and a classifier trained on handcrafted features, according to an example embodiment.

FIG. 9 illustrates a graph 900 comparing the performances of a classifier trained on handcrafted features, a fully connected 5-layer neural network, and a deep convolutional neural network, according to an example embodiment. In this example, the classifier trained on handcrafted feature—illustrated by line 902—is the Variant Quality Score Recalibration (VQSR), a tool of the Genome Analysis Toolkit (GATK) that evaluates the likelihood of a read pileup window being a false positive variant call on the basis of handcrafted features. The 5-layer fully connected neural network—illustrated by line 904—is provided as a reference for comparison purposes. The deep convolutional neural network pipeline—illustrated by line 906—depicts the performance of an example pipeline (e.g., pipeline 200 and/or pipeline 300) as described above. Note that graph 900 illustrates the false discovery rate for INDEL calling; however, other false variants (e.g., SNPs, CNVs, etc.) may also be detected.

In graph 900, the horizontal axis is the false positive discovery rate; the larger the discovery rate, the greater number of false positives that are detected. The vertical axis is the sensitivity setting of the variant caller, where a larger number indicates a higher level of sensitivity (i.e., more true variants and more false variants detected).

As illustrated in the graph 900, the false discovery rate of all three tools increases as the sensitivity increases. However, the false discovery rate of the fully connected 5-layer neural network and the deep convolutional neural network pipeline continues to increase as sensitivity increases beyond the false discovery rate of VQSR. Thus, deep learning models (both single neural networks or a pipeline of two or more neural networks) outperforms VQSR in detecting false positives and provide more accurate confidence intervals.

X. GENOTYPING USING NEURAL NETWORKS

Generally, the process of variant discovery from whole genome sequencing data involves sequencing a sample, aligning the sequence reads, identifying variants sites from those sequence reads, and evaluating the likelihood that those variant sites are true variants or false positive detections. In addition to these operations, analysis pipelines disclosed herein may genotype the detected variants.

Consider a simple example for detecting and genotyping a SNP. A reference genome may specify that a particular position in the genome has a nucleotide base of "G". At that position, a sequenced sample genome may contain multiple sequence reads (e.g., 30 sequence reads) that overlap at that position in the genome. If all of the sequence reads have a "G" nucleotide base at that location, the genotype of that sample may be a "homozygous reference." If some of the sequence reads have a "G" nucleotide base at that location, and other sequence reads have a "T" nucleotide base at that location, the genotype of that sample may be a "heterozygous variant." If all of the sequence reads have a "T" nucleotide base at that location, then the genotype of that sample may be a "homozygous variant." Thus, for each variant (e.g., SNP, INDEL, CNV, etc.) may also have an associated genotype (e.g., heterozygous SNP, homozygous SNP, etc.).

An analysis pipeline may pass along information about the confidence levels of various determinations or evaluations. A DNA sequencer may output a confidence level for each of the sequenced base pairs in the sequence reads. A sequence alignment tool may output a confidence level for each sequence read indicating the likelihood that the alignment of that sequence read with respect to a reference genome is correct. A variant caller may output a confidence level for each potential variant site indicating the type of variant detected, the likelihood that the variant type is accurate, and/or the likelihood that identified variant is a true variant. In such a pipeline, few absolute determinations may be made; rather, statistical estimations of accuracy may provide context for each stage in the analysis, impacting downstream analyses and informing subsequent processing on how to interpret the data.

Figure 11:
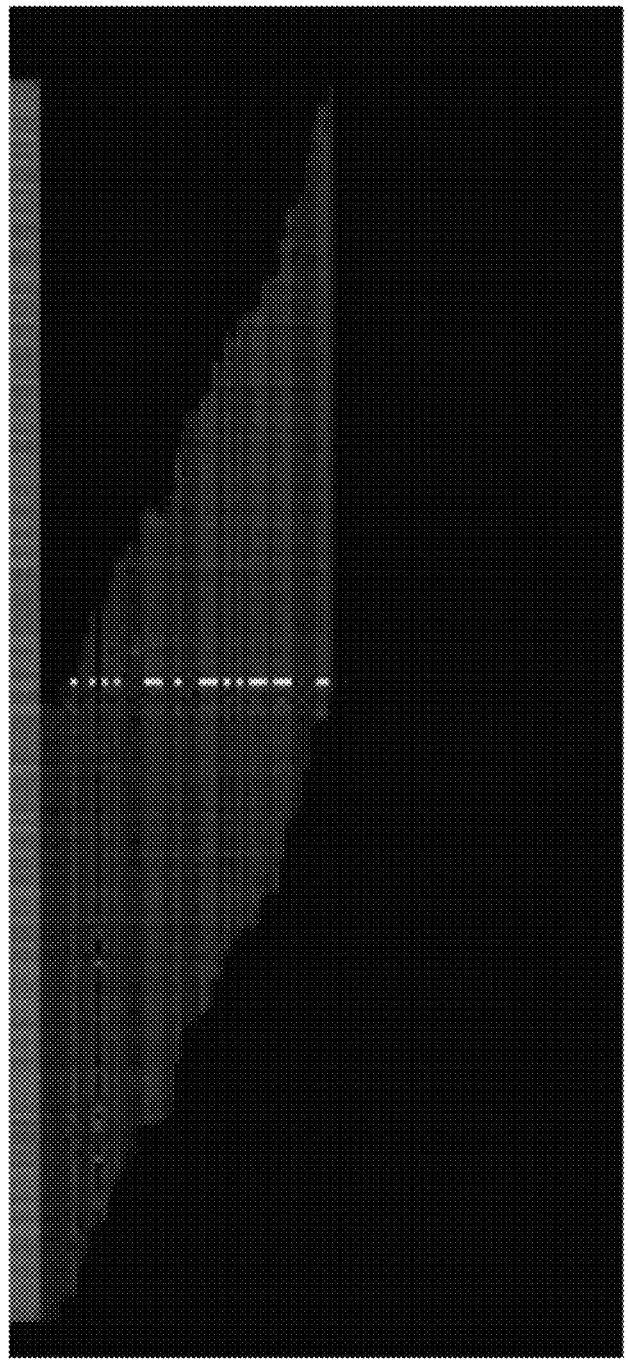
FIG. 11 depicts an example image representing a read pileup window containing a SNP with allele highlighting, according to an example embodiment.

In addition to the pipelined variant caller described above, the present application also describes using neural networks for modeling variant genotyping. A neural network may be trained using images constructed from data representing read pileup windows that span across alleles. Within an image, overlapping sequence reads that agree with a particular allele may be highlighted or otherwise visually distinguished from base pairs that are different from that particular allele. FIG. 11 depicts an example image representing a read pileup window containing a SNP with allele highlighting, according to an example embodiment. By training a neural network (e.g., using data from a reference genome) to detect image patterns representative of homozygous references, heterozygous variants, and homozygous variants, a deep learning model may be generated and applied to other read pileup windows. The trained model may determine, based on an image representing a read pileup window of an allele from a different sample, the model may calculate the likelihood that the allele is a homozygous reference, the likelihood that the allele is a heterozygous variant, and the likelihood that the allele is homozygous variants. Each likelihood may represent a confidence level that the allele is the associated genotype.

In some implementations, a classification layer of a neural network may carry out a regression on the three likelihood values and generate a quality score. For example, a sum of the likelihood that the allele is a heterozygous variant (p(HET)) and of the likelihood that the allele is a homozygous variant (p(HOM_VAR)) may represent the likelihood that the allele is a variant (p(var)); this likelihood may be the same as or proportionally related to the quality score for the allele. Represented mathematically, this quality score determination may be written as follows:

$$QUAL = p(\text{var}) = p(\text{HET}) + p(\text{HOM\_VAR})$$

An example pipeline may include a highly sensitive allele caller, a pileup image generator, a stage for performing allele determination, and a stage for genotype labeling. The highly sensitive caller may call individual alleles in the sample (as opposed to calling sites). This enables a genotype label to be assigned to an allele, even in scenarios where multiple alleles could be present at single nucleotide position. In genotyping pipelines, an allele may serve as the context for processed (as opposed to a variant site in the variant caller pipelines described above).

Then, for each allele, a pileup image generator may construct a graphical representation of the read pileup window of a particular allele. In some embodiments, the highly sensitive caller may label particular nucleotide locations within the read pileup window based on the associated allele. Based on read sequence data, confidence information associated with the read sequence data, a reference genome, and the allele nucleotide position labels (or lack thereof), the pileup image generator may produce images for each alleles containing features that distinguish sequence reads that match the allele from reads that don't match the allele. FIG. 11 illustrates an example heterozygous SNP read pileup window.

Then, at the stage for performing allele determination, a trained neural network may evaluate the generated read pileup images and evaluate the likelihood that the images represent homozygous references, heterozygous variants, or homozygous variants. These likelihoods may be output as numerical values representing a confidence level or a percentage likelihood, for example. Collectively, determining these likelihood values may be referred to as "genotype labeling."

If the neural network is untrained and the pileup images provided to the network are training data, then an additional stage may involve applying training a classification layer of the neural network based using labels corresponding to the training pileup images. For example, pileup images from a reference genome associated with known heterozygous variants may be labeled as heterozygous variants. Training the neural network with these labels may produce a model capable of distinguishing between homozygous references, heterozygous variants, and homozygous variants (and for assigning likelihood values indicating the confidence that a particular allele is a certain genotype).

Figure 12:
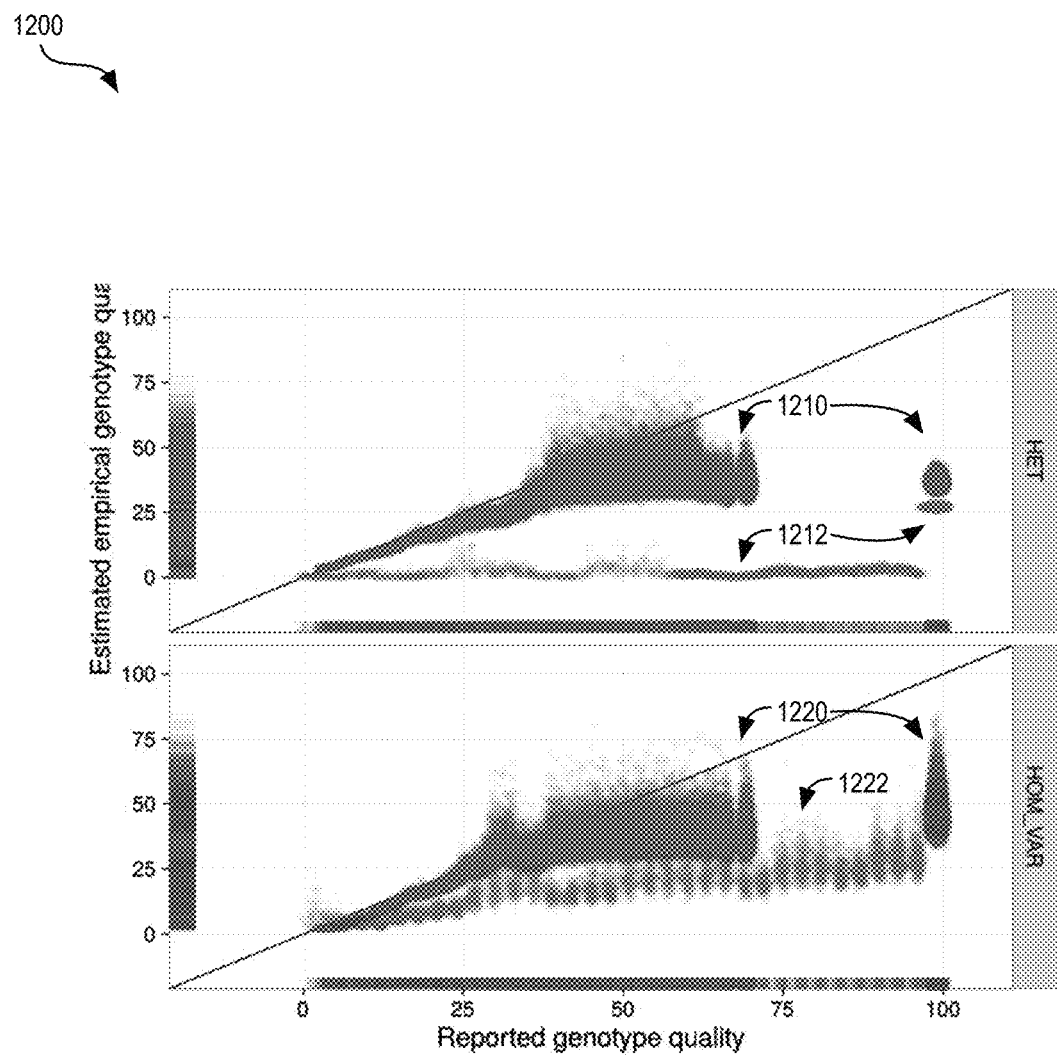
FIG. 12 illustrates graphs 1200 that compare genotype quality determinations performed with the GATK HaplotypeCaller to genotype quality determinations performed with a deep learning genotype model.

FIG. 12 illustrates graphs 1200 that compare genotype quality determinations performed with the GATK HaplotypeCaller to genotype quality determinations performed with a deep learning genotype model. In the top graph, the estimated empirical genotype quality scores (on a scale from 0 to 100) generated using the deep learning genotyper 1210 are substantially better than the estimated empirical genotype equality scores generated using the GATK HaplotypeCaller 1212. The top graph illustrates genotype quality scores for heterozygous variants.

Likewise, on the bottom graph, the estimated empirical genotype quality scores (on a scale from 0 to 100) generated using the deep learning genotyper 1220 are substantially better than the estimated empirical genotype equality scores generated using the GATK HaplotypeCaller 1222. The bottom graph illustrates genotype quality scores for homozygous variants. As shown in the graphs 1200, the deep learning model significantly outperforms the genotyping carried out using more traditional machine learning processes.

Figure 13:
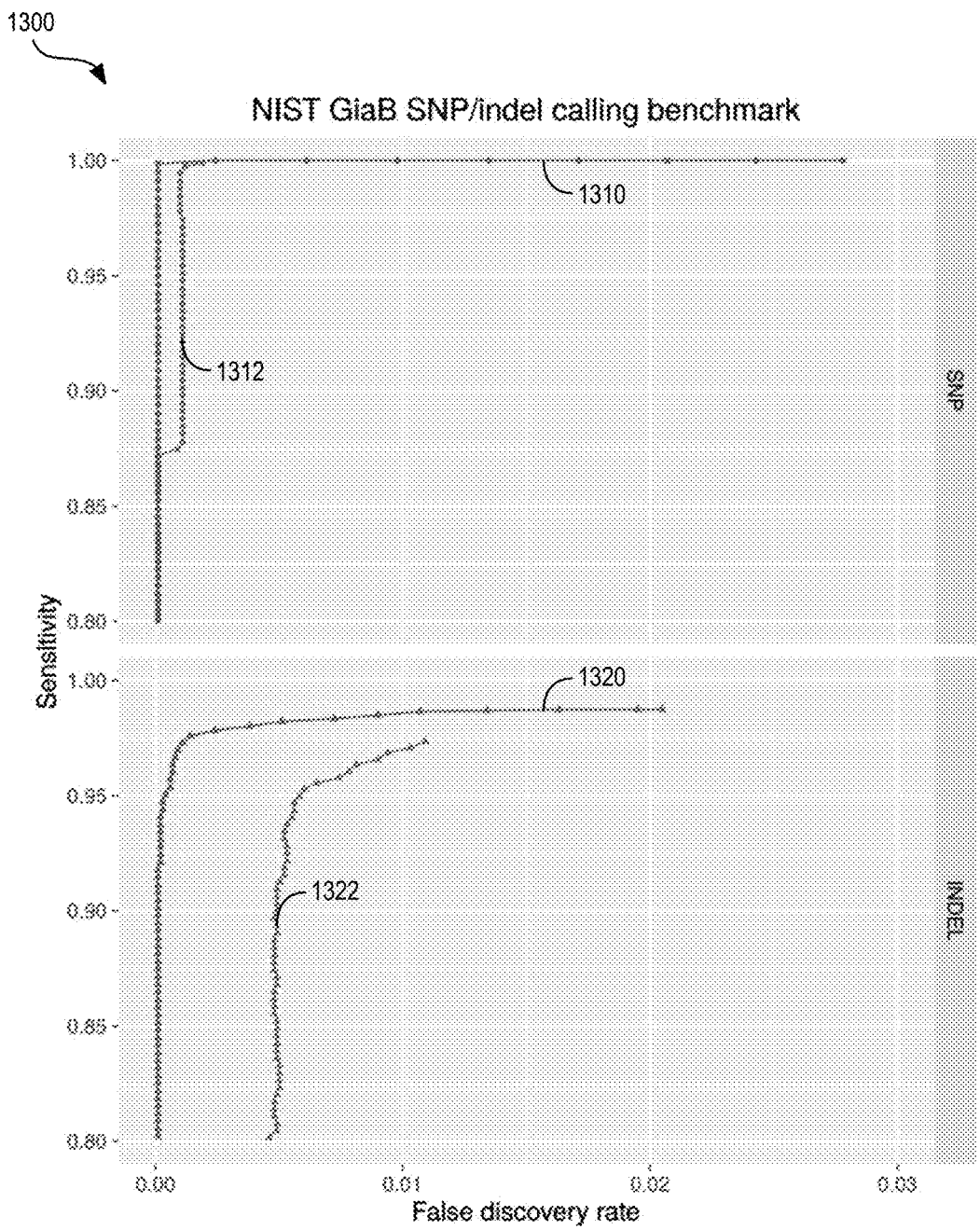
FIG. 13 illustrates graphs 1300 that compare SNP and INDEL calling performance between the GATK HaplotypeCaller and the deep learning genotyper.

FIG. 13 illustrates graphs 1300 that compare SNP and INDEL calling performance between the GATK HaplotypeCaller and the deep learning genotyper. The top graph, which illustrates SNP false discovery rate against sensitivity, illustrates the deep learning genotyper 1310 outperforming the SNP false discovery rate of the GATK HaplotypeCaller 1312. Likewise, the bottom graph, which depicts the INDEL false discovery rate against sensitivity, illustrates the deep learning genotyper 1320 substantially outperforming the GATK HaplotypeCaller 1322.

XI. EXAMPLE METHODS

Figure 10:
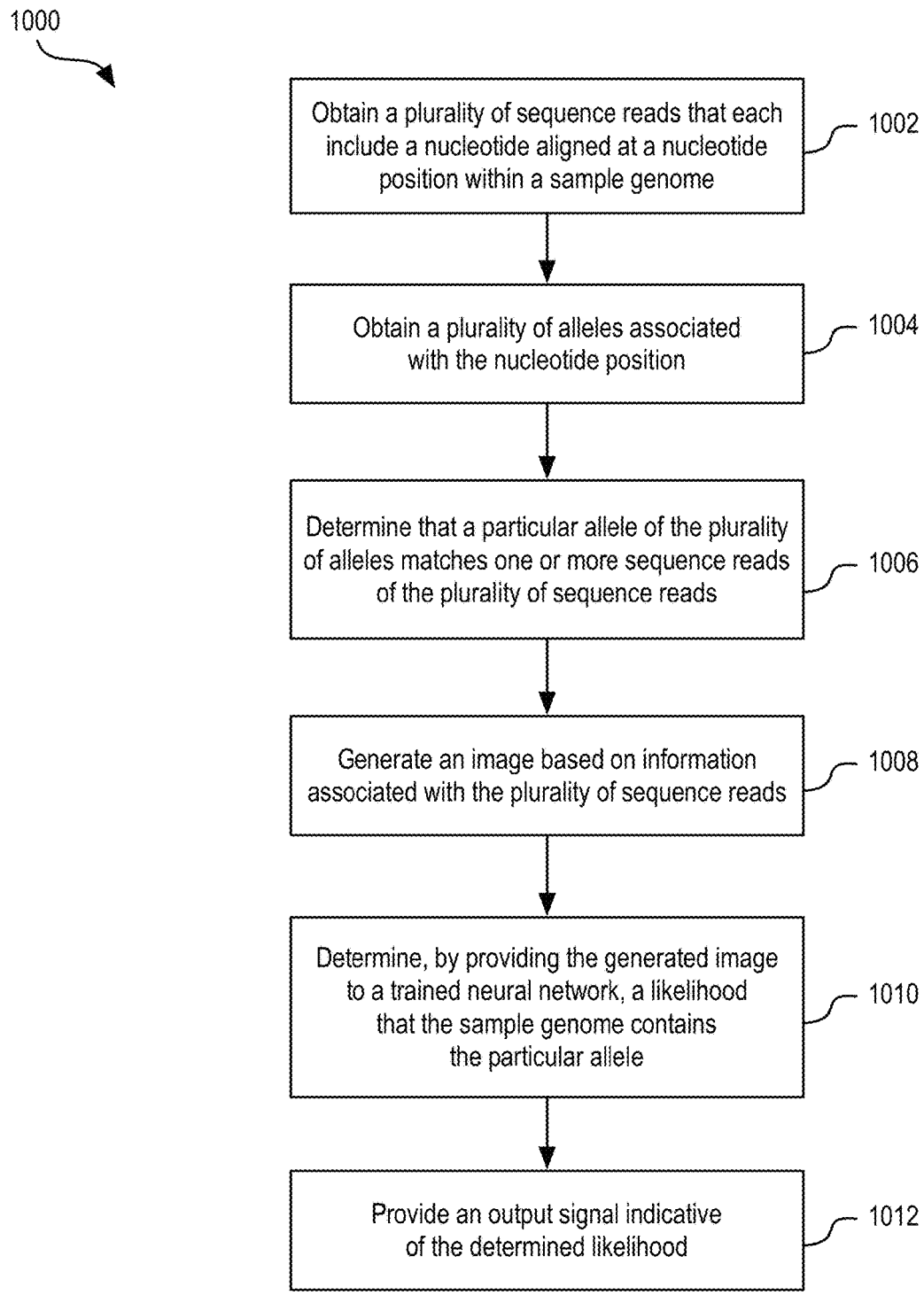
FIG. 10 is a flowchart of operations 1000, according to an example implementation.

FIG. 10 is a flowchart of operations 1000, according to an example implementation. Operations 1000 may include one or more actions as illustrated by blocks 1002-1010. Although the blocks are illustrated in sequential order, these blocks may also be performed in parallel, and/or in a different order than those described herein. Also, the various blocks may be combined into fewer blocks, divided into additional blocks, and/or removed based upon the directed implementation.

In addition, the operations 1000 and other operations disclosed herein show functionality of one possible implementation. In this regard, each block may represent a module, a segment, or a portion of program code, which includes one or more instructions executable by a processor or computing device for implementing specific logical operations or steps. The program code may be stored on any type of computer-readable medium, for example, such as a storage device included in a disk or hard drive. The computer-readable medium may include a non-transitory computer-readable medium, for example, such as computer-readable media that stores data for short periods of time like register memory, processor cache and/or random access memory (RAM). The computer-readable medium may also include non-transitory media, such as secondary or persistent long-term storage, like read-only memory (ROM), optical or magnetic disks, and compact-disc read-only memory (CD-ROM), for example. The computer-readable media may be considered a computer-readable storage medium, for example, or a tangible storage device.

In addition, one or more blocks in FIG. 10 may represent circuitry that is wired to perform the specific logical operations.

A. Obtain a Plurality of Sequence Reads

Block 1002 involves obtaining a plurality of sequence reads that each include a nucleotide aligned at a nucleotide position within a first sample genome. The sequence reads may each include a nucleotide sequence aligned at a reference nucleotide position within the sample genome. The sequence reads may be text or graphical representations of unaligned or aligned read data spanning across a range of nucleotide positions in the sample genome.

Each sequence read may contain metadata indicating the manner in which the first sample was sequenced (i.e., which read process was used), parameters of that read process, quality scores for each base pair, and any other information. The first sample genome may be data associated with a reference genome (e.g., NA12878, among other reference genomes).

B. Obtain a Plurality of Alleles Associated with the Nucleotide Position

Block 1004 involves obtaining a plurality of alleles associated with the nucleotide position. The particular nucleotide position may be a location within a gene or a chromosome. Based on previous human (or another organism) genome studies, one or more known alleles may exist at that nucleotide position. Sequence reads containing a nucleotide base at that nucleotide position may collectively indicate whether or not each of those alleles is present in the sample genome.

The plurality of alleles may be stored, for example, in one or more databases indexed by the nucleotide position (e.g., position 1,000,000 on chromosome 1). Obtaining these alleles may involve querying the database or otherwise retrieving data indicating of the alleles from memory or a data storage device.

C. Determine that a Particular Allele Matches One or More Sequence Reads

Block 1006 involves determining that a particular allele of the plurality of alleles matches one or more sequence reads of the plurality of sequence reads, wherein the particular allele is located at the nucleotide position. A sequence read may "match" a particular allele if the nucleotide bases in the sequence read that align with the particular allele are the same nucleotide bases of that allele. If multiple overlapping sequence reads match a particular allele, a deep learning network may output a high likelihood that the particular allele is present within the sample genome.

D. Generate an Image Based on Information Associated with the Plurality of Sequence Reads Block 1008 involves generating an image based on information associated with the plurality of sequence reads. Each nucleotide position may be converted into pixel data which is mapped to an image. Training a deep learning network may involve using unsupervised learning to detect patterns or features in the images representative of the read pileup windows. Then, using the labels, a classification layer (or separate classifier) may be trained using supervised learning to classify those patterns and features as either representing true variants or false positive variant calls. The colors and pixel locations of the image may represent information about candidate alleles and/or candidate variants, along with information about how many sequence reads agree or disagree with those candidate alleles.

E. Determine a Likelihood that the Sample Genome Contains a Particular Allele

Block 1010 involves determining, by providing the generated image to a trained neural network, a likelihood that the sample genome contains the particular allele. The neural network may receive the image as an input and may characterize that image to detect features and patterns in the image. Some images may contain features or patterns indicative of false candidate alleles, while other images may contain features or patterns indicative of true candidate alleles. By training a neural network to detect and weigh these distinguishing features, the neural network may evaluate the generated image and determine a likelihood that the candidate allele represented in the generated image is a true candidate allele (i.e., that the particular allele is present within the sample genome).

F. Providing an Output Signal Indicative of the Determined Likelihood

Block 1012 involves providing an output signal indicative of the determined likelihood. In some instances, the likelihoods may be stored in a database or table on a storage medium. In other instances, the likelihoods may be output to computing systems or other analysis pipelines to serve as a basis for genotyping the second sample genome, conducting medical diagnoses, or otherwise be used in a study involving genomes from multiple organisms. In some embodiments, the likelihoods may be processed to identify sources of error in the read process used to generate the sequence reads in the read pileup windows.

XI. CONCLUSION

It should be understood that arrangements described herein are for purposes of example only. As such, those skilled in the art will appreciate that other arrangements and other elements (e.g. machines, interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. It is also to be understood that the terminology used herein is for the purpose of describing particular implementations only, and is not intended to be limiting.

What is claimed is:

1. A method comprising:
obtaining a plurality of sequence reads that each include a nucleotide aligned at a nucleotide position within a sample genome;
obtaining a plurality of alleles associated with the nucleotide position;
determining that a particular allele of the plurality of alleles matches one or more sequence reads of the plurality of sequence reads, wherein the particular allele is located at the nucleotide position;
generating an image based on information associated with the plurality of sequence reads;
determining, by providing the generated image to a trained neural network, a likelihood that the sample genome contains the particular allele; and
providing an output signal indicative of the determined likelihood.

2. The method of claim 1, wherein the trained neural network is a convolutional neural network.

3. The method of claim 1, wherein the plurality of alleles are data objects specifying one or more of the following: (i) a position in the sample genome, (ii) a label, and (iii) a type of variant.

4. The method of claim 3, further comprising:
upon determining that the particular allele of the plurality of alleles matches one or more sequence reads, appending the number of matching sequence reads to the data object associated with the particular allele.

5. The method of claim 3, further comprising:
upon determining that the particular allele of the plurality of alleles matches one or more sequence reads, appending a number of disambiguating sequence reads that indicate a presence of unknown alleles at the nucleotide position to the data object associated with the particular allele.

6. The method of claim 1, wherein generating the image comprises:
generating color information for a plurality of pixels that collectively form the image, wherein the color information includes a plurality of color channels, wherein a first color channel represents a nucleotide base type, a second color channel represents a quality score, and a third color channel represents a presence of a nucleotide base.

7. The method of claim 1, wherein the output signal indicative of the determined likelihood includes data stored in a variant call format (VCF).

8. The method of claim 1, wherein the plurality of sequence reads is a first plurality of sequence reads, and wherein the method further comprises:
performing, for a second plurality of sequence reads that each include a nucleotide aligned at a second nucleotide position within the sample genome, the operations of (i) obtaining the plurality of sequence reads, (ii) obtaining the plurality of alleles, (iii) determining that the particular allele of the plurality of alleles matches one or more sequence reads of the plurality of sequence reads, (iv) generating the image, (v) determining the genotype likelihoods and probability of being an error, and (vi) providing the output signal in parallel with the operations for the first plurality of sequence reads.

9. A method comprising:
obtaining a plurality of sequence reads that each include a nucleotide aligned at a nucleotide position within a sample genome, wherein the sequence reads are aligned to a reference genome according to a first alignment;
receiving a variant call at the nucleotide position and associated with the sample genome, wherein the variant call includes a first confidence value indicative of a likelihood that the sample genome contains a variant specified by the variant call at the nucleotide position;
determining that the nucleotide position is located within a region of ambiguity;
responsive to receiving the variant call at the nucleotide position and determining that the nucleotide position is located within the region of ambiguity, realigning one or more sequence reads of the plurality of sequence reads, wherein the realignment causes the sequence reads to be aligned to the reference genome according to a second alignment; and
providing an output signal indicative of the second alignment.

10. The method of claim 9, wherein determining that the nucleotide position is located within a region of ambiguity comprises:
obtaining a set of variant calls at positions adjacent to the nucleotide position that include a respective set of confidence values, wherein the positions of the set of variant calls define the region of ambiguity;
determining that the average of the set of confidence values is below a threshold level of confidence; and
based on the determination that the average of the set of confidence values is below the threshold level of confidence, labeling the nucleotide position as being within the region of ambiguity, wherein labeling the nucleotide position as being within the region of ambiguity causes execution of the realignment.

11. The method of claim 9, wherein realigning the one or more sequence reads comprises:
performing a local string graph assembly procedure on the plurality of sequence reads to determine one or more potential haplotypes; and
realigning the plurality of sequence reads based on the one or more potential haplotypes.

12. The method of claim 11, wherein performing the local string graph assembly procedure comprises providing the plurality of sequence reads to a De Bruijn graph.

13. The method of claim 9, further comprising:
based on the second alignment, determining a second confidence value indicative of a likelihood that the sample genome contains the variant specified by the variant call at the nucleotide position after realignment, wherein the output signal includes the second confidence value.

14. A non-transitory computer-readable medium having instructions stored thereon that, upon execution by at least one processor, causes performance of operations comprising:
   obtaining a plurality of sequence reads that each include a nucleotide aligned at a nucleotide position within a sample genome;
   obtaining a plurality of alleles associated with the nucleotide position;
   determining that a particular allele of the plurality of alleles matches one or more sequence reads of the plurality of sequence reads, wherein the particular allele is located at the nucleotide position;
   generating an image based on information associated with the plurality of sequence reads;
   determining, by providing the generated image to a trained neural network, a likelihood that the sample genome contains the particular allele; and
   providing an output signal indicative of the determined likelihood.

15. The non-transitory computer-readable medium of claim 14, wherein the trained neural network is a convolutional neural network.

16. The non-transitory computer-readable medium of claim 14, wherein the plurality of alleles are data objects specifying one or more of the following: (i) a position in the sample genome, (ii) a label, and (iii) a type of variant.

17. The non-transitory computer-readable medium of claim 16, further comprising:
   upon determining that the particular allele of the plurality of alleles matches one or more sequence reads, appending the number of matching sequence reads to the data object associated with the particular allele.

18. The non-transitory computer-readable medium of claim 16, further comprising:
   upon determining that the particular allele of the plurality of alleles matches one or more sequence reads, appending a number of disambiguating sequence reads that indicate a presence of unknown alleles at the nucleotide position to the data object associated with the particular allele.

19. The non-transitory computer-readable medium of claim 14, wherein the output signal indicative of the determined likelihood includes data stored in a variant call format (VCF).

20. The non-transitory computer-readable medium of claim 14, wherein the plurality of sequence reads is a first plurality of sequence reads, and wherein the method further comprises:
   performing, for a second plurality of sequence reads that each include a nucleotide aligned at a second nucleotide position within the sample genome, the operations of (i) obtaining the plurality of sequence reads, (ii) obtaining the plurality of alleles, (iii) determining that the particular allele of the plurality of alleles matches one or more sequence reads of the plurality of sequence reads, (iv) generating the image, (v) determining the likelihood, and (vi) providing the output signal in parallel with the operations for the first plurality of sequence reads.

* * * * *

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 1
acacacacac                                                          10

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
gtcattgacc gagtcag                                                  17

<210> SEQ ID NO 3
<211> LENGTH: 69
<212> TYPE: DNA
<213> ORGANISM: Artificial Sequence
<220> FEATURE:
<223> OTHER INFORMATION: Synthetic oligonucleotide
```

-continued

```
<400> SEQUENCE: 3
cggtgaggat gctcggccag gtcccacctc ccaccgggga cccagaagca ggggcggcgt      60
ccgctcact                                                             69
```